US006355780B1

(12) United States Patent
Wallach et al.

(10) Patent No.: US 6,355,780 B1
(45) Date of Patent: Mar. 12, 2002

(54) ANTIBODIES TO THE DEATH DOMAIN MOTIFS OF REGULATORY PROTEINS

(75) Inventors: David Wallach, Rehovot (IL); Mark P. Boldin, Moscow (RU); Eugene E. Varfolomeev, Rehovot (IL); Zeev Pancer, Mainz (DE); Igor Mett, Rehovot; Tanya M. Goncharov, Ashkelon, both of (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 08/894,626

(22) PCT Filed: Feb. 15, 1996

(86) PCT No.: PCT/US96/02326

§ 371 Date: Dec. 9, 1997

§ 102(e) Date: Dec. 9, 1997

(87) PCT Pub. No.: WO96/25941

PCT Pub. Date: Aug. 29, 1996

(30) Foreign Application Priority Data

Feb. 22, 1995 (IL) .................................................. 112742
Sep. 13, 1995 (IL) .................................................. 115289

(51) Int. Cl.[7] ........................ C07K 16/00; A61K 39/42; A61K 39/395
(52) U.S. Cl. ............................... 530/389.1; 530/388.1; 530/388.22; 424/139.1; 424/143.1
(58) Field of Search ........................... 530/350, 388.22, 530/388.23, 389.2, 388.1, 389.1; 424/143.1, 145.1, 158.1, 139.1; 435/70.21

(56) References Cited

U.S. PATENT DOCUMENTS

| | | | | | |
|---|---|---|---|---|---|
| 5,359,037 A | * | 10/1994 | Wallach et al. | ......... | 530/388.22 |
| 5,563,039 A | * | 10/1996 | Goeddel et al. | ............ | 435/7.1 |
| 5,674,234 A | * | 10/1997 | Leder et al. | ............. | 435/252.3 |
| 5,712,381 A | * | 1/1998 | Lin et al. | ..................... | 536/23.5 |
| 5,830,469 A | * | 11/1998 | Lynch et al. | ............. | 424/144.1 |
| 5,837,817 A | * | 11/1998 | Aggrawal et al. | .......... | 530/350 |
| 5,843,675 A | * | 12/1998 | Lin et al. | ..................... | 435/7.1 |
| 5,847,099 A | * | 12/1998 | Lin et al. | ..................... | 536/23.5 |
| 5,849,501 A | * | 12/1998 | Lin et al. | ..................... | 435/7.1 |
| 5,852,173 A | * | 12/1998 | Lin et al. | ..................... | 530/350 |
| 5,856,161 A | * | 1/1999 | Aggrawal et al. | .......... | 435/196 |
| 5,869,612 A | * | 2/1999 | Goeddel et al. | ............ | 530/350 |
| 6,042,826 A | * | 3/2000 | Cauligiuri et al. | ........ | 424/130.1 |

FOREIGN PATENT DOCUMENTS

| | | |
|---|---|---|
| EP | 0568925 | 11/1993 |
| WO | 9531544 | 11/1995 |
| WO | WO96/12735 | 5/1996 |
| WO | WO96/30404 | 10/1996 |
| WO | WO96/31603 | 10/1996 |
| WO | WO96/36730 | 11/1996 |

OTHER PUBLICATIONS

Delalanty et l, *J Immunol,* (1997), V90(3) p. 383 (Abst).*
Crabtree et al, *J. Invest Dermotal* 1997 108 (2) p. 215.*
Srinivasata et al, *J.BC* 1997, 272 (30) p. 18542.*
Vandevoorde et al, *J. Cell Biol* 1997 137 (7) p. 1627.*
Wang et al, *Gene Therapy* 1997 4(5), p. 432.*
Marsters et al *Curr Biol* 1996, 6(6)p. 750.*
Yang et al, *Cell,* 1997, 89(7) p. 1067.*
Medema et al, *EMBO J* 16(10) pp. 2794–2801.*
Screator et al, *PNAS,* 1997 94(9) pp. 4615–4619.*
Duan et al, *Nature* 1997, p. 86, 385(6611).*
Haller et al *Immunity* 1997, 7(6) p. 831.*
Itoh, N. et al., J. Biol. Chem. 1993, vol. 268, pp. 10932–10937.*
Hsu et al., "The TNF Receptor 1–Associated Protein TRADD Signals Cell Death and NF–B Activation", *Chemtracts–Biochemistry and Molcular Biology,* 5:321–323 (1994).
Itoh et al., "A Novel Protein Domain Required for Apoptosis", *The Journal of Biological Chemistry* 268:15:10932–10937, (1993).
Brakebusch et al., "Cytoplasmic truncation of the p55 tumour necrosis factor (TNF) receptor abolishes signalling, but not induced shedding of the receptor", *The EMBO Journal,* 11:3:943–950, (1992).
Tartaglis et al., "A Novel Domain within the 55 kd TNF Receptor Signals Cell Death" *Cell,* 74:845–853, (1993).
Gagliardini, Valeria et al., "Pervention of vertebrate neuronal death by the crma gene," *Science,* vol. 263 pp. 826–828 (Feb. 11, 1994).
Feinstein et al., "The death domain: a module shared by proteins with diverse cellular functions.", *TIBS,* vol. 20, pp. 342–344 (Sep. 1995).
Clement, Marie–Veronique et al., "Fas and tumor necrosis factor receptor–mediated cell death: similarities and distinctions." *J. Exp. Med.,* vol. 180, pp. 557–567 (Aug. 1994).

(List continued on next page.)

*Primary Examiner*—Yvonne Eyler
*Assistant Examiner*—Janet L. Andres
(74) *Attorney, Agent, or Firm*—Browdy and Neimark

(57) ABSTRACT

A modulator of regulatory cellular events occurring intracellularly which are mediated by regulatory proteins containing a "death domain" motif is provided. The "death domain" is a regulatory portion of the regulatory proteins, and the modulator is capable of interacting with one or more "death domain" motifs contained in the regulatory proteins and affecting the regulatory action of one or more of the regulatory proteins. The modulator preferably is capable of interating with "death domain" motifs within p55-TNF-R, FAS/APO1-R, NGF-R, MORT-1, RIP, TRADD, or ankryin, as illustrated in the Figure. A method for producing the modulators is also provided. The modulators are useful for modulating functions mediated in cells by proteins containing the "death domain".

6 Claims, 4 Drawing Sheets

OTHER PUBLICATIONS

Song, Ho Yeong et al., "Aggregation of the intracellular domain of the type I tumor necrosis factor receptor defined by the two–hybrid system.", The Journal of Biological Chemistry, vol. 269, No. 36, pp. 22492–22495 (1994).

Boldin, Mark P. et al., "A novel protein that interacts with the death domain of fas/apo1 contains a sequence motif related to the death domain.", The Journal of Biological Chemistry, vol. 270, No. 14, pp. 7795–7798 (1995).

Boldin, Mark P. et al., "Self–association of the "Death Domains" of the p55 tumor necrosis factor (tnf) receptor and fas/apo1 prompts signaling for tnf and fas/apo1 effects." The Journal of Biological Chemistry, vol. 270, No. 1, pp. 387–391 (Jan. 1995).

Hsu, Hailing et al., "The tnf receptor 1–associated protein tradd signals cell death and nf–kb activation." Cell, vol. 81, pp. 495–504 (May 1995).

Chinnaiyan, Arul M. et al., "FAAD, a novel death domain––containing protein, interacts with the death domain of fas and initiates apoptosis.", Cell, vol. 81, pp. 505–512 (May 1995).

Stanger, Ben Z. et al., "RIP: a novel protein containing a death domain that interacts with fas/apo1 (cd95) in yeast and causes cell death.", Cell, vol. 81, pp. 513–523 (May 1995).

* cited by examiner

FIG. 1

```
Fas/APO1     VKGFVRKNGVNEAKIDEIKNDNVQDTAEQKVQLLRNWHQLHGKKEA.YDILIKDEKKANLCTLA              307
Ankyrin1     WAELAREIQFSVEDINRIRVENPNSLLEQSVALLNIWVIREGQN.ANMENLYTALQSIDRGEIV              1479
p55 TNF-R    WKEFVRRLGLSDHEIDRLELQNGRCLREAQYSMLATWRRRTPRREATLELLGRVLRDHDLGCL              434
NGF-R        WRHLAGELGYQPEHIDSFTHE.....ACPVRALLASWA...TQDSATLDALIAALRRIQRADLV              414
MORT1        WRRLARQLKVSDTKIDSIEDRYPRNLIERVRESLRIWKN.TEKENATVAHLVGALRSCQMN.LV              210
```

FIG. 2

| DBD CONSTRUCT | AD CONSTRUCT | SCORE | lpr^cg-like mutation effect | | |
|---|---|---|---|---|---|
| | | | IN DBD CONSTRUCT | IN AD CONSTRUCT | IN BOTH |
| p55 | p55 | ■ | | | |
| Fas | Fas | ■ | | | |
| TRADD | TRADD | ■ | ND | ND | ND |
| MORT1 | MORT1 | | | | |
| RIP | RIP | ■ | ■ | | |
| TRADD | p55 | ■ | ND | | ND |
| p55 | TRADD | ■ | | ND | ND |
| TRADD | Fas | | ND | | ND |
| Fas | TRADD | | | ND | ND |
| MORT1 | p55 | | | | |
| p55 | MORT1 | | | | |
| MORT1 | Fas | ■ | ■ | | |
| Fas | MORT1 | ■ | | ▒ | |
| RIP | p55 | ▒ | | | |
| p55 | RIP | ▒ | | | |
| RIP | Fas | | | | |
| Fas | RIP | ▒ | | | |
| TRADD | MORT1 | | ND | | ND |
| MORT1 | TRADD | ■ | ■ | ND | ND |
| TRADD | RIP | ■ | ND | ▒ | ND |
| RIP | TRADD | ■ | | ND | ND |
| MORT1 | RIP | ■ | ■ | ■ | ■ |
| RIP | MORT1 | ■ | ■ | | |

<1 h.    1-2h    2-24h    NEGATIVE

ANTIBODIES TO THE DEATH DOMAIN MOTIFS OF REGULATORY PROTEINS

FIELD OF THE INVENTION

The present invention is generally in the field of regulatory proteins which exert their effects by intracellular signaling processes which are mediated by regulatory elements (domains or motifs) contained within the intracellular domains of these proteins. More specifically, the present invention concerns new modulators being proteins, peptides, antibodies or analogs or fragments of any thereof, and organic compounds which are capable of interacting with, or binding to the newly discovered 'death domain' motif present in a wide range of related and unrelated proteins, for example, receptors of the TNF/NGF family such as p55 TNF-R, FAS-R, NGF-R, a related protein MORT-1, proteins known as TRADD and RIP and the unrelated protein ankyrin 1. These new modulators are capable of modulating or regulating the activity of the proteins which contain the 'death domain' motif.

BACKGROUND OF THE INVENTION AND PRIOR ART

There is a very large group of regulatory proteins which exert their regulatory effects on cells by way of intracellular signaling processes, mediated by regulatory portions or motifs contained within these proteins. Members of this group of proteins include, receptors belonging to the TLF/NGF family of receptors, such as, for example, the p55 and p75 TNF receptors (p55 and p75 TNF-Rs), the NGF receptor (NGF-R) and the Fas/APO1 protein (also called the FAS-ligand receptor or FAS-R, and hereinafter will be called FAS-R); these receptors being characterized by having an extracellular ligand-binding domain, a transmembrane domain and an intracellular (IC) domain, which intracellular domain, or portions thereof, is involved in the mediation of the intracellular signaling events initiated by the binding of the ligand to the extracellular domain. Other members of this group include various intracellular proteins, for example, the cytoskeleton-associated structural proteins, the ankyrins, which have a regulatory domain that is possibly involved in the ability of these proteins to associate with or bind to other cytoskeletal proteins, e.g. spectrin, or to other transmembrane proteins. Yet another member of this group is the recently identified MORT1 protein (also called HF1, see co-pending IL 112002 and EL 112692), which is capable of binding specifically to the intracellular domain of the FAS-R, and which is also capable of self-association and of mediating, in a ligand-independent manner, cytotoxic effects on cells. In MORT-1, a regulatory domain was also identified (see IL 112692).

Tumor Necrosis Factor (TNF-α) and Lymphotoxin (TNF-β) (hereinafter, TNF, refers to both TNF-α and TNF-β) are multifunctional pro-inflammatory cytokines formed mainly by mononuclear phagocytes, which have many effects on cells (Wallach, D. (1986) in: Interferon 7 (Ion Gresser, ed.), pp. 83–122, Academic Press, London; and Beutler and Cerami (1987)). Both TNF-α and TNF-β initiate their effects by binding to specific cell surface receptors. Some of the effects are likely to be beneficial to the organism: they may destroy, for example tumor cells or virus infected cells and augment antibacterial activities of granulocytes. In this way, TNF contributes to the defense of the organism against tumors and infectious agents and contributes to the recovery from injury. Thus, TNF can be used as an anti-tumor agent in which application it binds to its receptors on the surface of tumor cells and thereby initiates the events leading to the death of the tumor cells. TNF can also be used as an anti-infectious agent.

However, both TNF-α and TNF-β also have deleterious effects. There is evidence that over-production of TNF-α can play a major pathogenic role in several diseases. Thus, effects of TNF-α, primarily on the vasculature, are now known to be a major cause for symptoms of septic shock (Tracey et al., 1986). In some diseases, TNF may cause excessive loss of weight (cachexia) by suppressing activities of adipocytes and by causing anorexia, and TNF-α was thus called cachetin. It was also described as a mediator of the damage to tissues in rheumatic diseases (Beutler and Cerami, 1987) and as a major mediator of the damage observed in graft-versus-host reactions (Piquet et al., 1987). In addition, TNF is known to be involved in the process of inflammation and in many other diseases.

Two distinct, independently expressed, receptors, the p55 and p75 TNF-Rs, which bind both TNF-α and TNF-β specifically, initiate and/or mediate the above noted biological effects of TNF. These two receptors have structurally dissimilar intracellular domains suggesting that they signal differently (See Hohmann et al., 1989; Engelmann et al., 1990; Brockhaus et al., 1990; Loetscher et al., 1990; Schall et al., 1990; Nophar et al., 1990; Smith et al., 1990; and Heller et al., 1990). However, the cellular mechanisms, for example, the various proteins and possibly other factors, which are involved in the intracellular signaling of the p55 an p75 TNF-Rs have yet to be elucidated (In IL 109632 there are described for the first time, new proteins capable of binding to the intracellular domains of p55 and p75 TNF-Rs, these intracellular domains being called, respectively, p75IC and p55 IC). It is this intracellular signaling, which occurs usually after the binding of the ligand, i.e. TNF (α or β), to the receptor, that is responsible for the commencement of the cascade of reactions that ultimately result in the observed response of the cell to TNF.

As regards the above mentioned cytocidal effect of TNF, in most cells studied so far, this effect is triggered mainly by the p55 TNF-R. Antibodies against the extracellular domain (ligand binding domain) of the p55 TNF-R can themselves trigger the cytocidal effect (see EP 412486) which correlates with the effectivity of receptor cross-linking by the antibodies, believed to be the first step in the generation of the intracellular signaling process. Further, mutational studies (Brakebusch et al., 1992; Tartaglia et al., 1993) have shown that the biological function of the p55 TNF-R depends on the integrity of its intracellular domain, and accordingly it has been suggested that the initiation of intracellular signaling leading to the cytocidal effect of TNF occurs as a consequence of the association of two or more intracellular domains of the p55 TNF-R. Moreover, TNF (α and β) occurs as a homotrimer and as such has been suggested to induce intracellular signaling via the p55 TNF-R by way of its ability to bind to and to cross-link the receptor molecules, i.e. cause receptor aggregation. In co-pending IL 109632 and IL 111125, there is described how the p55IC and p55DD can self-associate and induce, in a ligand-independent fashion, TNF-associated effects in cells.

Another member of the TNF/NGF superfamily of receptors is the FAS receptor (FAS-R) which has also been called the Fas antigen, a cell-surface protein expressed in various tissues and sharing homology with a number of cell-surface receptors including TNF-R and NGF-R. The FAS-R mediates cell death in the form of apoptosis (Itoh et al., 1991), and appears to serve as a negative selector of autoreactive T cells, i.e. during maturation of T cells, FAS-R mediates the apoptopic death of T cells recognizing self-antigens. It has also been found that mutations in the FAS-R gene (lpr) cause a lymphoproliferation disorder in mice that resembles the human autoimmune disease systemic lupus erythematosus (SLE) (Watanabe-Fukunaga et al., 1992). The ligand for the FAS-R appears to be a cell-surface associated molecule carried by, amongst others, killer T cells (or cytotoxic T lymphocytes—CTLs), and hence when such CTLs contact cells carrying FAS-R, they are capable of inducing apoptopic cell death of the FAS-R-carrying cells. Further, a monoclonal antibody has been prepared that is specific for FAS-R, this monoclonal antibody being capable of inducing apoptopic cell death in cells carrying FAS-R, including mouse cells transformed by cDNA encoding human FAS-R (Itoh et al., 1991).

It has also been found that various other normal cells, besides T lymphocytes, express the FAS-R on their surface and can be killed by the triggering of this receptor. Uncontrolled induction of such a killing process is suspected to contribute to tissue damage in certain diseases, for example, the destruction of liver cells in acute hepatitis. Accordingly, finding ways to restrain the cytotoxic activity of FAS-R may have therapeutic potential.

Conversely, since it has also been found that certain malignant cells and HIV-infected cells carry the FAS-R on their surface, antibodies against FAS-R, or the FAS-R ligand, may be used to trigger the FAS-R mediated cytotoxic effects in these and thereby provide a means for combating such malignant cells or HFV-infected cells (see Itoh et al., 1991). Finding yet other ways for enhancing the cytotoxic activity of FAS-R may therefore also have therapeutic potential.

In co-pending IL 109632, IL 111125 and IL 112002 there is described that the intracellular domain of FAS-R, the so-called FAS-IC, is capable of self-association and contains within this intracellular domain a region called the 'death domain' (DD) which is primarily responsible for the self-association of the FAS-IC. This 'death domain' shares sequence homology with the p55 TNF-R, 'death domain' (p55DD).

It has been a long felt need to provide a way for modulating the cellular response to TNF ($\alpha$ or $\beta$) and FAS-R ligand, for example, in pathological situations as mentioned above, where TNF or FAS-R ligand is over-expressed it is desirable to inhibit the TNF- or FAS-R ligand-induced cytocidal effects, while in other situations, e,g. wound healing applications, it is desirable to enhance the TNF effect, or in the case of FAS-F, in tumor cells or HIV-infected cells it is desirable to enhance the FAS-R mediated effect.

A number of approaches have been made by the present inventors (see for example, European Application Nos. EP 186833, EP 308378, EP 398327 and EP 412486) to regulate the deleterious effects of TNF by inhibiting the binding of TNF to its receptors using anti-TNF antibodies or by using soluble TNF receptors (being essentially the soluble extracellular domains of the receptors) to compete with the binding of TNF to the cell surface-bound TNF-Rs. Further, on the basis that TNF-binding to its receptors is required for the TNF-induced cellular effects, approaches by the present inventors (see for example IL 101769 and its corresponding EP 568925) have been made to modulate the TNF effect by modulating the activity of the TNF-Rs. Briefly, EP 568925 (IL 101769) relates to a method of modulating signal transduction and/or cleavage in TNF-Rs whereby peptides or other molecules may interact either with the receptor itself or with effector proteins interacting with the receptor, thus modulating the normal functioning of the TNF-Rs. In EP 568925 there is described the construction and characterization of various mutant p55 TNF-Rs, having mutations in the extracellular, transmembranal, and intracellular domains of the p55 TNF-R. In this way regions within the above domains of the p55 TNF-R were identified as being essential to the functioning of the receptor, i.e. the binding of the lizand (TNF) and the subsequent signal transduction and intracellular signaling which ultimately results in the observed TNF-effect on the cells. Further, there is also described a number of approaches to isolate and identify proteins, peptides or other factors which are capable of binding to the various regions in the above domains of the TNF-R, which proteins, peptides and other factors may be involved in regulating or modulating the activity of the TNF-R. A number of approaches for isolating and cloning the DNA sequences encoding such proteins and peptides; for constructing expression vectors for the production of these proteins and peptides; and for the preparation of antibodies or fragments thereof which interact with the TNF-R or with the above proteins and peptides that bind various regions of the TNF-R, are also set forth in EP 568925. However, no description is made in EP 568925 of the actual proteins and peptides which bind to the intracellular domains of the TNF-Rs (e.g. p55 TNF-R), nor is any description made of the yeast two-hybrid approach to isolate and identify such proteins or peptides which bind to the intracellular domains of TNF-Rs. Similarly, heretofore there has been no disclosure of proteins or peptides capable of binding the intracellular domain of FAS-R.

Thus, when it is desired to inhibit the effect of TNF, or the FAS-R ligand, it would be desirable to decrease the amount or the activity of TNF-Rs or FAS-R at the cell surface, while an increase in the amount or the activity of TNF-Rs or FAS-R would be desired when an enhanced TNF or FAS-R ligand effect is sought. To this end the promoters of both the p55 TNF-R and the p75 TNF-R have been sequenced, analyzed and a number of key sequence motifs have been found that are specific to various transcription regulating factors, and as such the expression of these TNF-Rs can be controlled at their promoter level, i.e. inhibition of transcription from the promoters for a decrease in the number of receptors, and an enhancement of transcription from the promoters for an increase in the number of receptors (see IL 104355 and EL 109633). Corresponding studies concerning the control of FAS-R at the level of the promoter of the FAS-R gene have yet to be reported.

Further, it should also be mentioned that, while it is known that the tumor necrosis factor (TNF) receptors, and the structurally-related receptor FAS-R, trigger in cells, upon stimulation by leukocyte-produced ligands, destructive activities that lead to their own demise, the mechanisms of this triggering are still little understood. Mutational studies indicate that in FAS-R and the p55 TNF receptor (p55-R) signaling for cytotoxicity involve distinct regions within their intracellular domains (Brakebusch et al., 1992; Tartaglia et al., 1993; Itoh and Nagata, 1993). These regions (the 'death domains') have sequence similarity. The 'death domains' of both FAS-R and p55-R tend to self-associate. Their self-association apparently promotes that receptor aggregation which is necessary for initiation of signaling (see IL 109632, IL 111125 and IL 1 12002, as well as Song et al., 1994; Wallach et al., 1994; Boldin et al., 1995) and at high levels of receptor expression can result in triggering of ligand-independent signaling (IL 109632, IL 111125 and Boldin et al., 1995).

The ankyrins constitute a family of proteins that control interactions between integral membrane components and cytoskeletal elements and are found in a wide range of tissues such as brain tissue and in erythrocytes, the erythrocyte ankyrin being the best characterized. The ankyrins are intracellular proteins associated with the cytoskeletal elements of the cell and have three domains: an upper domain involved in binding to the intracellular domains of transmembrane proteins, this upper domain containing the well-known repeats, the so-called ankyrin repeats; a middle domain which is involved in binding to spectrin, i.e. the binding of spectrin to transmembrane proteins via the ankyrins; and a C-terminal or lower (or third) domain, which is the regulatory domain that is capable of being phosphorylated, this domain regulating the activity of the other two domains when phosphorylated or dephosphorylated. This latter regulatory domain also has three parts: a middle part that can be deleted by alternative splicing naturally, and hence some ankyrins have this Part and others don't; and two other parts, less-well characterized (for a review on the ankyrins, see Lux et al., 1990 and Lambert and Bennett, 1993).

It should be noted however, as is set forth hereinbelow, that in accordance with the present invention, it has been discovered that the upper part of the above noted regulatory (C-terminal) domain of ankyrin contains a so-called 'death domain' motif, which may function to mediate the binding of proteins together (activity of the first two ankyrin domains), or may function conformationally to regulate the arkyrin protein.

The NGF-R is a low affinity NGF receptor which is not well characterized. The NGF-R is considered to be involved in growth regulation, such as its possible involvement in signaling intracellularly for NGF-induced effects. However, a recent publication discloses that overexpression of NGF-R in the absence of NGF can cause cell death. Thus, NGF-R appears to have a regulatory role in cell viability (see Rabizadeh et al. 1993).

It should be noted however, as is set forth hereinbelow, that in accordance with the present invention, it has been discovered that the NGF-R contains a 'death domain' motif in its intracellular domain, which may be involved in the mediation of the intracellular events associated with the regulatory role played by NGF-R with regards to cell viability.

MORT-1 is a recently discovered protein that binds to the intracellular domain of FAS-R, is capable of self-association and can activate cell cytotoxicity on its own. Hence, MORT1 is also a regulatory protein involved in intracellular signaling processes. It was also discovered that MORT-1 has a 'death domain' motif that is associated with its observed biological activity (see co-pending IL 112002 and IL 112692).

Two further intracellular proteins, RIP (Stanger et al., 1995) and TRADD (Hsu et al., 1995), that bind to the intracellular domains of p55 TNF-R or FAS-R and apparently take part in the induction of their cytocidal effect, have recently been cloned. All three proteins, MORT-1, RIP and TRADD, were found to contain the sequence motif shared between the 'death domains' of the intracellular domains of p55-TNF-R and FAS-R. As in the receptors, the 'death domain' motifs (DD) in the three intraceuular proteins seem to be sites of protein-protein interaction. The three proteins interact with the p55-TNF-R and FAS-R intracellular domains by the binding of their DDs to those in the receptors, and in both TRADD and RIP (though not in MORT-1) the DDs self-associate. It has now been found that MORT-1 and TRADD bind differentially to FAS-R and p55 TNF-R and also bind to each other. Moreover, both bind effectively to RIP.

Interference of the interaction between the above three intracellular proteins will result in modulation of the effects caused by this interaction. Thus, inhibition of TRADD binding to MORT-1 may modulate FAS-R-p55 TNF-R intraction. Inhibition of RIP in addition to the above inhibition of TRADD binding to MORT-1 may further modulate FAS-R-p55 TNF-R interaction.

Monoclonal antibodies raised against the 'death domain' of the p55 TNF-R, specifically against the binding site or sites of TRADD and RIP can also be used to inhibit or prevent binding of these proteins and thus cause modulation of the interaction between the FAS-R and the p55 TNF-R.

In a way analogous to that noted above in respect of TNFJNF-R and FAS-ligand/FAS-R, there is also a need to provide a way for modulating the activity of the above noted proteins, i.e. ankyrin, NGF-R and MORT-1, namely, to inhibit their activity when it is associated with detrimental effects, e.g. disease/disorder-related cell cytotoxicity or conformational changes in cell-shape; or to enhance their activity when this is desired, e.g. for directed destruction of diseased cells, etc.

In the co-pending applications, IL 109632, IL 111125, EL 112002 and IL 112692, there are described proteins which are involved in the modulation of the activity of receptors belonging to the TNF/NGF receptor family, these proteins being characterized by being capable of binding/associating with the intracellular domains of one or more of these receptors.

The present invention concerns modulators such as proteins, peptides, antibodies and organic compounds which are capable of interacting/binding with one or more so-called 'death domain' motifs in the intracellular domains of proteins containing such motifs, these proteins being related, e.g. members of the TNF/NGF receptor family or proteins related thereto, e.g. MORT1, or unrelated proteins, e.g. ankyrins. These modulators are characterized by recognizing general structural features common to the 'death domain' motifs of the 'death domain' motif-containing proteins, and by also recognizing specific structural features present in each of the different 'death domain' motifs of these proteins.

Accordingly, it is one aim of the invention to provide modulators, as noted above, capable of binding to or interacting with the 'death domain' motifs of one or more of the 'death domain' motif-containing proteins and thereby modulating the activity of these proteins.

Another aim of the invention is to provide antagonists (e.g. antibodies) to one class of these modulators, namely the naturally-occurring proteins or peptides which bind to 'death domain' motif-containing proteins, and which antagonists may be used to inhibit the signaling process, when desired, when such 'death domain' motif-binding proteins or peptides are positive signal effectors (i.e. induce signaling), or to enhance the signaling process, when desired, when such 'death domain' motif-binding proteins are negative signal effectors (i.e. inhibit signaling).

Yet another aim of the invention is to use such 'death domain' motif-binding proteins or peptides to isolate and characterize additional proteins or factors, which may, for example, be involved further downstream in the signaling process, and/or to isolate and identify other receptors further upstream in the signaling process to which these 'death domain' motif-binding proteins bind, and hence, in whose function they are also involved.

Moreover, it is an aim of the present invention to use the above-mentioned 'death domain' motif-binding proteins as antigens for the preparation of polyclonal and/or monoclonal antibodies thereto. The antibodies. in turn, may be used for the purification of the new 'death domain' motif-binding proteins from different sources, such as cell extracts or transformed cell lines.

Furthermore, these antibodies may be used for diagnostic purposes, e.g. for identifying disorders related to abnormal functioning of cellular effects mediated by the various proteins belonging to the group of 'death domain' motif-containing proteins.

A further aim of the invention is to provide pharmaceutical compositions comprising the above 'death domain' motif-binding modulators (proteins, peptides, organic molecules), and pharmaceutical compositions comprising the 'death domain' motif-binding protein or peptide antagonists, for the treatment or prophylaxis of conditions related to the activity of the 'death domain' motif-containing proteins, for example, such compositions can be used to enhance the TNF or FAS ligand effect or effects mediated by NGF-R, MORT-1, RIP, TRADD and ank-yrin, or to inhibit the TNF or FAS ligand effect or effects mediated by depending on the above noted nature of the 'death domain' motif-binding modulators or antagonists thereof contained in the composition.

A still further aim of the invention is to use the various 'death domain' motifs of the proteins containing them for the design and synthesis of complementary peptides and organic molecules which will be modulators of these proteins.

SUMMARY OF THE INVENTION

The present invention is based on the surprising and unexpected finding that there exists a so-called 'death domain' motif in a wide range of proteins some of which are related and others which are not related. For example, this 'death domain' motif has been found in p55 TNF-R, FAS-R, NGF-R, MORTI, RIP and TRADD which are related to each other, as well as in the unrelated protein, ankyrin 1.

As noted above, the 'death domain' motif of the proteins containing this motif is located in the intracellular regulatory domain of these proteins. Hence, the 'death domain' motif appears to be involved in a regulatory function associated with cell viability (cell death) as well as cell shape/conformation, this function being effected at (i.e. in the case of receptors containing this motif) or close to (i.e. in the case of structural intracellular proteins, e.g. ankyrin) the cell surface. Moreover, the observation, in accordance with the present invention, that the 'death domain' motif is conserved amongst a wide range of related and non-related proteins indicates that this motif may have an important regulatory function.

Accordingly, the present invention provides a modulator of regulatory cellular events occurring intracellularly that are mediated by regulatory proteins containing a 'death domain' motif which is a regulatory portion of said proteins, said modulator being capable of interacting with one or more of the 'death domain' motifs contained in said regulatory proteins and affecting the regulatory action of one or more of said regulatory proteins.

In particular, the present invention provides:

(i) a modulator is selected from the group comprising naturally-derived 'death domain' motif-binding proteins and peptides and analogs and derivatives thereof capable of interacting with one or more of said 'death domain' motifs;

(ii) a modulator is selected from the group of synthetically produced complementary peptides, synthesized by using as substrates the 'death domain' motif sequences of said regulatory proteins containing 'death domain' motifs, said complementary peptides being capable of interacting with one or more of said 'death domain' motifs.

(iii) a modulator is selected from the group comprising antibodies or active fragments thereof capable of interacting with one or more of said 'death domain' motifs.

(iv) a modulator is selected from the group of organic compounds capable of interacting with one or more of said 'death domain' motifs, said organic compounds being derived from known compounds and selected by using said 'death domain' motifs as a substrate in a binding assay, or being synthesized using said 'death domain' motifs as a substrate for designing and synthesizing said organic compounds.

(v) a modulator is selected from the group of peptides or polypeptides derived from naturally occurring 'death domain' motif sequences, said peptides or polypeptides being capable of interacting with one or more of said 'death domain' motifs, and analogs and derivatives of said peptides or polypeptides capable of interacting with one or more of said 'death domain' motifs.

(vi) a modulator of any one of (i)–(v) wherein said modulator is further characterized by being capable of recognizing the general 'death domain' motif sequence features common to the 'death domain' motifs of 'death domain' motif containing proteins, and being capable of recognizing one or more of the specific 'death domain' motifs of said proteins, said specific sequence features being specific to each 'death domain' motif sequence of each of said proteins.

(vii) a modulator of any one of (i)–(vi) wherein said modulator is capable of interacting with one or more of the 'death domain' motifs contained within the proteins belonging to the group comprising p55 TNF-R, FAS-R, NGF-R, MORT-1, RIP, TRADD and ankyrin 1.

(viii) a modulator of (vii) wherein said modulator is further characterized by being capable of interacting with common sequence features of the 'death domain' motifs of said group of proteins, said common sequence features comprising the group of common amino acid residues W (tryptophan), L (leucine), I (isoleucine), A (alanine), D (aspartic acid), E (glutamic acid), T (threonine), R (arginine) and Y (tyrosine) at the location within said 'death domain' motifs shown in FIG. 1.

The present invention also provides a DNA sequence encoding a modulator being a protein, peptide or polypeptide or an analog of any one of (i), (ii) and (vii).

An embodiment of the DNA sequence of the invention is a DNA sequence encoding a naturally derived protein or peptide selected from the group consisting of:

(a) a cDNA sequence derived from the coding region of a native 'death domain' motif-binding protein or peptide, (b) DNA sequences capable of hybridization to a sequence of (a) under moderately stringent conditions and which encode a biologically active 'death domain' motif-binding protein or peptide; and (c) DNA sequences which are degenerate as a result of the genetic code to the DNA sequences defined in (a) and (b) and which encode a biologically active 'death domain' motif-binding protein or peptide.

Other embodiments of the DNA sequence of the invention are:

(i) DNA sequence encoding a 'death domain' motif-binding protein or peptide capable of binding to the 'death domain' motif of one or more of the proteins of the group comprising p55 TNF-R, FAS-R, NGF-R, MORT-1 and anlvrin 1.

(ii) DNA sequence encoding a peptide or polypeptide derived from the naturally occurring 'death domain' motif sequence of the 'death domain' motif-containing proteins.

(iii) DNA sequence encoding a peptide or polypeptide derived from the 'death domain' motif sequence of any one of the proteins of the group comprising p55 TNF-R, FAS-R, NGF-R, MORT-1, RIP, TRADD and ankyrin 1.

Furthermore, there is also provided:

(a) a protein, peptide or polypeptide and analogs of any one thereof encoded by a DNA sequence of the invention. said protein, peptide, polypeptide and analogs being capable of binding to or interacting with one or more of the 'death domain' motifs of one or more 'death domain' motif containing proteins.

(b) a vector comprising a DNA sequence of the invention.

(c) a vector of (b) capable of being expressed in a eukaryotic host cell.

(d) a vector of (b) capable of being expressed in a prokaryotic host cell.

(e) transformed eukaryotic or prokaryotic host cells containing a vector of (b), (c) or (d)

(f) a method for producing the protein, peptide, polypeptide or analogs of (a) comprising growing the transformed host cells of (e) under conditions suitable for the expression of said protein, peptide, polypeptide or analogs, effecting post-translational modifications of said protein, peptide, polypeptide or analogs as necessary for obtention thereof and extracting said expressed protein, peptide, polypeptide or analogs from the culture medium of said transformed cells or from cell extracts of said transformed cells.

(g) antibodies or active fragments or derivatives thereof, specific for the protein, peptide, polypeptide or analogs of (a).

The present invention also provides a method for the modulation of the TNF or FAS-R ligand effect on cells mediated by p55 TNF-R and FAS-R, or the functions mediated in cells by NGF-R, MORT-1, RIP, TRADD, ankyrin 1 or by other proteins containing a 'death domain' motif, comprising treating said cells with one or more proteins, peptides, polypeptides or analogs selected from the group consisting of the proteins, peptides, polypeptides or analogs of the invention (see (a) above), all being capable of binding to or interacting with the 'death domain' motif and modulating the activity of said 'death domain' motif-containing proteins, wherein said treating of said cells comprises introducing into said cells said one or more proteins, peptides, polypeptides or analogs in a form suitable for intracellular introduction thereof, or introducing into said cells a DNA sequence encoding said one or more proteins, peptides, polypeptides or analogs in the form of a suitable vector carrying said sequence, said vector being capable of effecting the insertion of said sequence into said cells in a way that said sequence is expressed in said cells.

An embodiment of the above method is a method wherein said treating of said cells is by transfection of said cells with a recombinant animal virus vector comprising the steps of:

(a) constructing a recombinant animal virus vector carrying a sequence encoding a viral surface protein (ligand) that is capable of binding to a specific cell surface receptor on the surface of said cell to be treated and a second sequence encoding a protein selected from the proteins, peptides, polypeptides and analogs of the invention, said protein, peptide, polypeptide or analogs, when expressed in said cells being capable of modulating the activity of said 'death domain' motif-containing protein; and (b) infecting said cells with said vector of (a).

Another method of the invention is a method for modulating the TNF or FAS-R ligand effect on cells mediated by p55 TNF-R and FAS-R, or the functions mediated in cells by NGF-R, MORT-1,RIP, TRADD, ankyrin 1 or by other proteins containing a 'death domain' motif, comprising treating said cells with antibodies or active fragments or derivatives thereof, of the invention (see (g) above), said treating being by application of a suitable composition containing said antibodies, active fragments or derivatives thereof to said cells, said composition being formulated for intracellular application.

Yet another method of the invention is a method for modulating the TNF or FAS-R ligand effect on cells mediated by p55 TNF-R and FAS-R, or the functions mediated in cells by NGF-R, MORT-1, RIP, TRADD, ankyrin 1 or by other proteins containing a 'death domain' motif, comprising treating said cells with an oligonucleotide sequence selected from a sequence encoding an antisense sequence of at least part of the sequence of the invention as noted above, said oligonucleotide sequence being capable of blocking the expression of at least one of the 'death domain' motif-binding proteins or peptides.

An embodiment of the above method is a method wherein said oligonucleotide sequence is introduced to said cells via a virus vector as noted above wherein said second sequence of said virus encodes said oligonucleotide sequence.

Other methods of the invention are:

(i) a method for treating tumor cells or HIV-infected cells or other diseased cells, comprising:
   (a) constructing a recombinant animal virus vector carrying a sequence encoding a viral surface protein that is capable of binding to a specific tumor cell surface receptor or HIV-infected cell surface receptor or receptor carried by other diseased cells and a sequence encoding a protein selected from the proteins, peptides, polypeptides and analogs of the invention, said protein, peptide, polypeptide or analogs when expressed in said tumor, HIV-infected, or other diseased cell being capable of killing said cell; and
   (b) infecting said tumor or HIV-infected cells or other diseased cells with said vector of (a).

(ii) a method for modulating the TNF or FAS-R ligand effect on cells mediaed by p55 TNF-R and FAS-R, or the fuinctions mediated in cells by NGF-R, MORT-1, RIP, TRADD, ankyrin 1 or by other proteins containing a 'death domain' motif, comprising applying the ribozyme procedure in which a vector encoding a ribozyme sequence capable of interacting with a cellular mRNA sequence encoding a protein or peptide of the invention, is introduced into said cells in a form that permits expression of said ribozyne sequence in said cells, and wherein when said ribozyme sequence is expressed in said cells it interacts with said cellular mRNA sequence and cleaves said mRNA sequence resulting in the inhibition of expression of said protein or peptide in said cells.

(iii) a method for isolating and identifying proteins, peptides, factors or receptors capable of binding to the 'death domain' motif-binding proteins or peptides of the invention, comprising applying the procedure of affinity chromatography in which said protein or peptide of the invention is attached to the affinity chromatography matrix, said attached protein is brought into contact with a cell extract and proteins, factors or receptors from cell extract which bound to said attached protein are then eluted, isolated analyzed.

(iv) a method for isolating and identifying proteins, capable of binding to the 'death domain' motif-binding proteins or peptides of the invention, comprising applying the yeast two-hybrid procedure in which a sequence encoding said 'death domain' motif-binding protein is carried by one hybrid vector and sequence from a cDNA or genomic DNA library are carried by the second hybrid vector, the vectors then being used to transform yeast host cells and the positive transformed cells being isolated, followed by extraction of the said second hybrid vector to obtain a sequence encoding a protein which binds to said 'death domain' motif-binding protein.

The present invention also provides a pharmaceutical composition for the modulation of the TNF- or FAS-R ligand- effect on cells mediated by p55 TNF-R and FAS-R, or the fuinctions mediated in cells by NGF-R, MORT-1, RIP, TRADD, ankyrin 1 or by other proteins containing a 'death domain' motif comprising, as active, ingredient a modulator of the invention.

Embodiments of the pharmaceutical compositions of the invention include:

(i) a pharmaceutical composition for modulating the TNF- or FAS-R ligand-effect on cells mediated by p55 TNF-R and FAS-R, or the functions mediated in cells by NGF-R, MORT-1, RIP, TRADD, ankyrin 1 or by other proteins containing a 'death domain' motif, comprising, as active ingredient, a recombinant animal virus vector encoding a protein capable of binding a cell surface receptor and encoding a protein or peptide or analogs thereof of the invention.

(ii) a pharmaceutical composition for modulating the TNF or FAS-R ligand effect on cells mediated by p55 TNF-R and FAS-R, or the functions mediated in cells by NGF-R, MORT-1, RIP, TRADD, ankyrin 1 or by other proteins containing a 'death domain' motif, comprising as active ingredient, an oligonucleotide sequence encoding an anti-sense sequence of the sequence of the invention.

A still further method of the invention is a method for isolating and identifying a protein capable of binding to the 'death domain' motifs of 'death domain' motif-containing proteins comprising applying the procedure of non-stringent southern hybridization followed by PCR cloning, in which a sequence or parts thereof of the invention is used as a probe to bind sequences from a cDNA or genomic DNA library, having at least partial homology thereto, said bound sequences then amplified and cloned by the PCR procedure to yield clones encoding proteins having at least partial; homology to said sequences of the invention.

In addition, the present invention also provides a method for designing drugs that are capable of modulating the activity of 'death domain' motif-containing proteins, comprising the procedures described herein in Examples 3 and 4.

Other aspects and embodiments of the present invention are also provided as arising from the following detailed description of the invention.

It should be noted that, where used throughout, the following terms "Modulation/Mediation of the TNF or FAS-R ligand effect on cells mediated by p55 TNF-R and FAS-R, or the flunctions mediated in cells by NGF-R, MORT1, RIP, TRADD, ankyrin 1 or by other proteins containing a 'death domain' motif are understood to encompass in vitro as well as in vivo treatment.

Moreover, where used throughout, the antibodies of the invention and the methods using these antibodies, include so-called "humanized" antibodies or the use thereof.

BRIEF DESCRIPTION OF THE DRAWINGS

FIG. 1 depicts schematically the sequence homology of the 'death domain' motif in MORT-1(SEQ ID NO:5), p55 TNF-R (SEQ ID NO:3), Fas/APO1 (FAS-R) (SEQ ID NO:1), low affinity NGF receptor (NGF-R) (SEQ ID NO:4) and the C-terminal part of the regulatory domain in ankyrin 1 (Ankyrin 1) (SEQ ID NO:2), as described in Example 1.

FIG. 2 depicts interactions of the 'death domains' of the p55-R, Fas/APOl, MORT1, TRADD and RIP in a yeast two-hybrid test, and the effect of lpr$^{cg}$-like mutations in these proteins on their interactions. Assessment of the interaction of Gal4 hybrid constructs encompassing the following human proteins, trunctated upstream to their DD motifs: p55-R (residues 326–426), FAS-R (residues 210–319), MORT-1 (residues 92–208), TRADD (residues 195–312) and RIP (residues 261–372), as well as of the following points mutants of these proteins: p55-R L35IN, FAS-R V238N, MORT-1 V121N, and RIP F308N, whose mutation sites within the DDs correspond to that found in the FAS-R of the Ipr$^{cg}$ mice. Each cDNA insert was introduced both into the Gal4 DNA binding domain (DBD) and the Gal4 activation domain (AD) constructs (pGBT9 abd pGAD-GH), and the binding of the inserts in both constructs to all other inserts within transfected SFY526 yeasts was assessed by a β-galactosidase expression filter assay. The results are presented in terms of the time required for development of strong color. ND—not done.

DETAILED DESCRIPTION OF THE INVENTION

Figure 3:
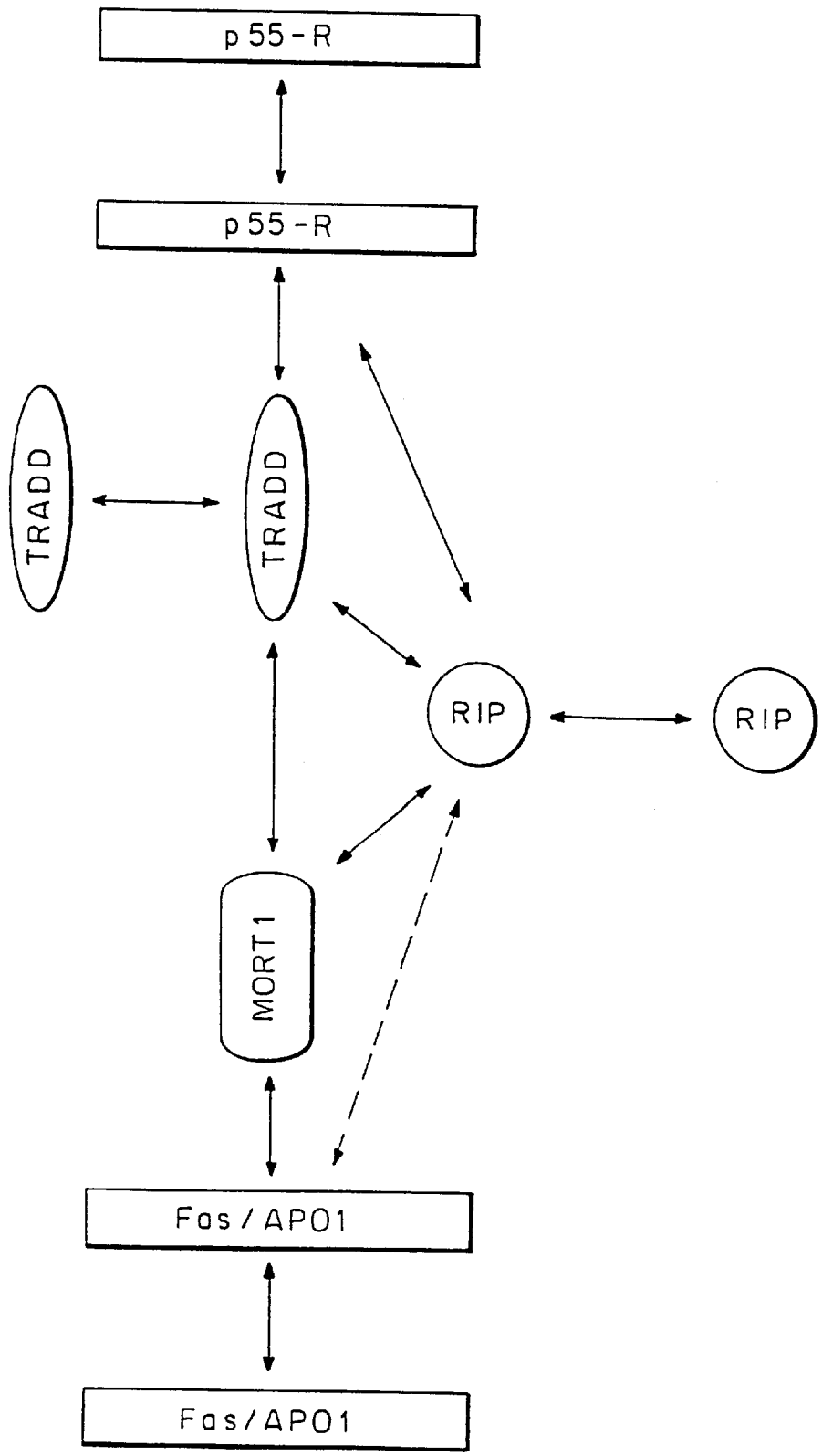
FIG. 3 is a diagrammatic illustration of the DD interactions observed in the yeast two-hybrid tests. The lengths and thicknesses of the arrows connecting the DD icons correspond to the intensity of the interactions, as observed in the experiment described in FIG. 2.

The present invention relates, in one aspect, to novel proteins or peptides which are capable of binding to one or more 'death domain' motifs of 'death domain' motif-containing proteins by virtue of recognizing sequence features common to the 'death domain' motifs within these proteins. Hence the 'death domain' motif binding proteins or peptides are considered as mediators or modulators of this group of 'death domain' motif-containing proteins. This group of 'death domain' motif-containing proteins includes: (i) members of the TNF/NGF receptor family such as, for example, p55 TNF-R, FAS-R (Fas/APO1) and the low affinity NGF receptor (NGF-R); (ii) other related proteins such as, for example, the recently discovered protein called MORT-1 (or HF1) (for "Mediator of Receptor-Mediated Toxicity") which, amongst its characteristics, is capable of self-association and specific binding to the intracellular domain of FAS-R; as well as (iii) apparently non-related proteins such as, for example, the cytoskeletal protein ankyrin 1. The 'death domain' motif and some of its characteristics has been disclosed in respect of the p55 TNF-R, FAS-R and MORT-1 in the co-pending Israel Application Nos. 109632, 111125, 112002 and 112692. The 'death domain' motif present in NGF-R and ankyrin 1 has been discovered in accordance with the present invention (see Example 1).

In the above noted co-pending applications there is described a number of proteins capable of binding specifically to the intracellular domains of p55-TNF-R and/or FAS-R, which proteins include MORT-1. However, in contrast, the present invention concerns, in this one aspect thereof, proteins or peptides which specifically bind to the 'death domain' motif of one or more of the above mentioned proteins belonging to the group characterized by having such a 'death domain' motif, the binding/interaction between the proteins or peptides of the invention and the 'death domain' motif being by virtue of sequence features common to the various 'death domain' motifs. Hence, the proteins or peptides of the invention are characterized by being capable of modulating or mediating the activity of one or more of the members of this group of proteins by recognizing features common to the 'death domain' motifs.

Accordingly, included in the present invention is a large group of proteins or peptides which bind to the various 'death domain' motifs, in which some of the proteins or peptides bind specific 'death domain' motifs of specific proteins or receptors, while others bind more than one such motif of more than one such protein/receptor. From FIG. 1 it arises that common sequence features of the 'death domain' motifs in 'death domain' motif-containing proteins such as p55 TNF-R, FAS-R, NGF-R, MORT1 and ankyrin 1 include common amino acid residues (residues marked within boxes) such as the W (tryptophan), L (leucine), I (isoleucine), A (alanine), D (aspartic acid) and E (glutamic acid), as well as T (threonine), R (arginine) and Y (tyrosine), at the location shown in FIG. 1.

The proteins or peptides of the invention may be obtained as described in the above noted co-pending patent applications (see also Example 3), by use of the yeast two-hybrid procedure in which the 'death domain' motif of, for example, p55-TNF-R, FAS-R, MORT-1, NGF-R, ankyrin 1 will be used as probes or 'baits' to isolate from genomic or cDNA libraries, clones expressing proteins or peptides capable of binding to one or more of these 'death domain' motifs. Alternatively, a synthetic DNA sequence can be synthesized in which there is included all of the common sequence features of the 'death domain' motifs of p55-TNF-R, FAS-R, MORT-1, NGF-R, ankyrin 1 (see FIG. 1), to provide a common or "universal" 'death domain' motif sequence. which in turn can be used in the yeast two-hybrid procedure to isolate and identify clones from cDNA or genoriic libraries which encode proteins or peptides capable of binding to this 'death domain' motif sequence.

Other approaches for obtaining the proteins and peptides of the invention include the well known standard procedures such as, for example, affinity chromatography in which, for example, peptides or protein fragments having the 'death domain' motif sequence of p55 TNF-R, FAS-R, MORTI, NGF-R and ankyrin 1; or a synthetically produced 'death domain' motif peptide having common sequence features of all the aforesaid 'death domain' motifs (see FIG. 1), are attached to the chromatography substrate or matrix and are brought into contact with cell extracts or lysates (of human/mammalian origin) and thereby proteins or peptides are isolated which are capable of binding to one or more of these 'death domain' motifs. Likewise, other standard chemical and recombinant DNA procedures usually employed for isolating proteins or peptides capable of binding to a specific amino acid sequence ('death domain' motif sequence) can be employed to obtain the proteins and peptides of the invention.

Thus, the present invention also concerns the DNA sequences encoding the proteins and peptides of the invention and the proteins and peptides encoded by these sequences.

Moreover, the present invention also concerns the DNA sequences encoding biologically active analogs and derivatives of these proteins and peptides of the invention, and the analogs and derivatives encoded thereby. The preparation of such analogs and derivatives is by standard procedure (see for example, Sambrook et al., 1989) in which in the DNA sequences encoding these proteins, one or more codons may be deleted, added or substituted by another, to yield analogs having at least a one amino acid residue change with respect to the native protein. Acceptable analogs are those which retain at least the capability of binding to the 'death domain' motif of one or more of the members of the above mentioned group of 'death domain' motif-containing proteins, or which can mediate any other binding or enzymatic activity, e.g. analogs which bind the 'death domain' motif but which do not signal, i.e. do not bind to a further downstream receptor, protein or other factor, or do not catalyze a signal-dependent reaction. In such a way analogs can be produced which have a so-called dominant-negative effect, namely, an analog which is defective either in binding to the, 'death domain' motif or in subsequent signaling following such binding. Such analogs can be used, for example, to inhibit the TNF, FAS-ligand-, NGF-R-mediated, MORT-1-mediated and ankyrin 1-mediated effect by competing with the natural IC-binding proteins.

Likewise, so-called dominant-positive analogs may be produced which would serve to enhance, for example, the TNF, FAS ligand. NGF-R-mediated, MORT-1-mediated and ankyrin 1- mediated effect. These would have the same or better 'death domain' motif-binding properties and the same or better signaling properties of the natural 'death domain' motif-binding proteins. Similarly, derivatives may be prepared by standard modifications of the side groups of one or more amino acid residues of the proteins, or by conjugation of the proteins to another molecule e.g. an antibody, enzyme, receptor, etc., as are well known in the art.

The new 'death domain' motif-binding proteins and peptides of the invention, e.g. the proteins and peptides capable of binding one or more of the 'death domain' motifs of p55 TNF-R, FAS-R, MORT-1, NGF-R and ankyrin 1, as well as RIP and TRADD, have a number of possible uses, for example:

(i) They may be used to mimic or enhance the function of TNF or FAS-R ligand, or the functions mediated by NGF-R, MORT-1, RIP, TRADD and ankyrin 1 or other proteins containing the 'death domain' motif, in situations where such an enhanced effect is desired such as in anti-tumor, anti-inflammatory, or anti-HIV or other disease/disorder applications where the enhanced activity is desired. In this case the proteins or peptides may be introduced to the cells by standard procedures known per se. For example, as the proteins or peptides are required to act intracellularly, i.e. bind/interact with intracellularly located 'death domain' motifs and it is desired that they be introduced only into the cells where their effect is wanted, a system for specific introduction of these proteins into the cells is necessary. One way of doing this is by creating a recombinant animal virus e.g. one derived from Vaccinia, to the DNA of which the following two genes will be introduced: the gene encoding a ligand that binds to cell surface proteins specifically expressed by the cells e.g. ones such as the AIDs (HIV) virus gp120 protein which binds specifically to some cells (CD4 lymphocytes and related leukemias), or a ligand that binds specifically to erythrocytes or nervous tissue (in the case of ankyrin 1), or a ligand binding specifically to cells characterized by expressing other members of the 'death domain' motif-containing group of proteins, e.g. those expressing MORT-1, RIP, TRADD, or any other ligand that binds specifically to cells carrying a TNF-R, FAS-R, or NGF-R such that the recombinant virus vector will be capable of binding such cells; and the gene encoding the new 'death domain' motif-binding protein or peptide. Thus, expression of the cell-surface-binding protein on the surface of the virus will target the virus specifically to the tumor cell, HIV-infected cells or other cells, following which the 'death domain' motif-binding protein or peptide encoding sequence will be introduced into the cells via the virus, and once expressed in the cells will result in enhancement of, for example, the TNF, FAS-R ligand, NGF-R-mediated, MORT-1-mediated, RIP- and TRADD-mediated, or ankyrin 1-mediated effect leading to, for example, the death of the tumor cells or other TNF-R- or FAS-R-carrying cells it is desired to kill. Construction of such recombinant animal virus is by standard procedures (see for example, Sambrook et al., 1989). Another possibility is to introduce the sequences of the new proteins or peptides in the form of oligonucleotides which can be absorbed by the cells and expressed therein.

(ii) They may be used to inhibit, for example, the TNF, FAS-R ligand, NGF-R-mediated, MORT1-mediated and aknyrin-l-mediated effect, e.g. in cases such as tissue damage in septic shock, graft-vs.-host rejection, acute hepatitis, or other diseases/disorders in which case it is desired to block the TNF-induced TNF-R, FAS-R ligand induced FAS-R or NGF induced NGF-R intracellular signaling or intracellular events mediated by MORT1, RIP, TRADD and ankyrin-1. In this situation it is possible, for example, to introduce into the cells, by standard procedures, oligonucleotides having the, anti-sense coding sequence for these new proteins or peptides which would effectively block the translation of mRNAs encoding these proteins and thereby block their expression and lead to the above noted desired inhibition of the effects mediated by the 'death domain' motif-containing proteins.

Such oligonucleotides may be introduced into the cells using the above recombinant virus approach, the second sequence carried by the virus being the oligonucleotide sequence. Another possibility is to use antibodies specific for these proteins or peptides to inhibit their intracellular signaling activity (via their binding to the 'death domain' motifs).

Yet another way of inhibiting the TNF FAS-R ligand, NGF-R-mediated, MORT-1-mediated, RIP- and TRADD-mediated, or ankyrin-1-mediated effect or effects mediated by other 'death domain' motif-containing proteins, is by the recently developed ribozyme approach. Ribozymes are catalytic RNA molecules that specifically cleave RNAs. Ribozymes may be engineered to cleave target RNAs of choice, e.g. the mRNAs encoding the new proteins or peptides of the invention. Such ribozymes would have a sequence specific for the mRNA of choice and would be capable of interacting therewith (complementary binding) followed by cleavage of the MRNA, resulting in a decrease (or complete loss) in the expression of the protein or peptide it is desired to inhibit, the level of decreased expression being dependent upon the level of ribozyme expression in the target cell. To introduce ribozymes into the cells of choice any suitable vector may be used, e.g. plasmid, animal virus (retrovirus) vectors, that are usually used for this purpose (see also (i) above, where the virus has, as second sequence, a cDNA encoding the ribozyme sequence of choice). Moreover, ribozymes can be constructed which have multiple targets (multi-target ribozymes) that can be used, for example, to inhibit the expression of one or more of the proteins or peptides of the invention (For reviews, methods etc. concerning ribozymes see Chen et al., 1992; Zhao and Pick, 1993; Shore et al., 1993; Joseph and Burke, 1993; Shimayama et al., 1993; Cantor et al., 1993; Barinaga, 1993; Crisell et al., 1993 and Koizumi et al., 1993).

(iii) They may be used to isolate, identify and clone other proteins or peptides which are capable of binding to them, e.g. other proteins or peptides involved in the intracellular signaling process that are downstream of the 'death domain' motif-containing proteins. In this situation, these options, namely, the DNA sequences encoding them may be used in the yeast two-hybrid system (see Example 2, below) in which the sequence of these proteins or peptides will be used as "baits" to isolate, clone and identify from cDNA or genomic DNA libraries other sequences ("preys") encoding proteins which can bind to these new 'death domain' motif-binding proteins. In the same way, it may also be determined whether the specific proteins or peptides of the present invention, namely, those which bind to the 'death domain' motif of p55 TNF-R, FAS-R, NGF-R, MORT-1 and ankyrin can bind to yet other receptors or proteins. Moreover, this approach may also be taken to determine whether the proteins or peptides of the present invention are capable of binding to other known receptors or proteins in whose activity they may have a functional role, i.e. other aas yet unidentified 'death domain' motif-containing receptors or proteins.

(iv) The new proteins may also be used to isolate, identify and clone other proteins of the same class i.e. those binding to 'death domain' motifs of the various receptors or proteins listed above or to functionally related receptors or proteins, and involved in their modulation/mediation. In this application the above noted yeast two-hybrid system may be used, or there may be used a recently developed (Wilks et al., 1989) system employing non-stringent southern hybridization followed by PCR cloning. In the Wilks et al. publication, there is described the identification and cloning of two putative protein-tyrosine kinases by application of non-stringent southern hybridization followed by cloning by PCR based on the known sequence of the kinase motif, a conceived kinase sequence. This approach may be used, in accordance with the present invention using the sequences of the new proteins or peptides to identify and clone those of related 'death domain' motif-binding proteins or peptides also capable of binding to 'death domain' motif-containing receptors or proteins.

(v) Yet another approach to utilizing the new proteins of the invention is to use them in methods of affinity chromatography to isolate and identify other proteins or factors to which they are capable of binding, e.g. other receptors related to TNF-Rs (TNF/NGF receptor superfamily) or other proteins or factors (e.g. related to MORT1, ankyrin 1) involved in the intracellular signaling or structural regulation process. In this application, the proteins of the present invention, may be individually attached to affinity chromatography matrices and then brought into contact with cell extracts or isolated proteins or factors suspected of being involved in the intracellular signaling or structural regulation process. Following the affinity chromatography procedure, the other proteins or factors which bind to the new proteins of the invention, can be eluted, isolated and characterized.

(vi) As noted above, the new proteins or peptides of the invention may also be used as inmmunogens (antigens) to produce specific antibodies thereto. These antibodies may also be used for the purposes of purification of the new proteins or peptides either from cell extracts or from transformed cell lines producing them. Further, these antibodies may be used for diagnostic purposes for identifying disorders related to abnormal functioning of, for example, the TNF, FAS-R ligand, NGF-R, MORT-1 or ankyrin 1 system, e.g. overactive or underactive TNF- or FAS-R ligand-induced cellular effect or NGF-R-, MORT-1- or ankyrin-1 mediated cellular effects. Thus, should such disorders be related to a malfunctioning intracellular signaling or structural regulation system involving the new proteins or antibodies, such antibodies would serve as an important diagnostic tool.

In another aspect, the present invention relates to complementary peptides which may be synthesized by well known standard procedures of the art, that are capable of binding or interacting specifically with one or more of the 'death domain' motifs of the above mentioned group of 'death domain' motif-containing proteins. These complementary peptides will be synthesized using, for example, the 'death domain' motif sequences of p55-TNF-R, FAS-R, MORT-1, RIP, TRADD, NGF-R, ankyrin 1, as substrates and synthesizing by standard chemical means peptides of sequence that are complementary to these 'death domain' motif sequences. A suitable complementary peptide is one that will be capable of binding to one or more of these 'death domain' motifs and thereby being capable of modulating or mediating the activity of 'death domain' motif-containing proteins.

The complementary peptides may be generated using as substrate one or more of the 'death domain' motif sequences set forth in FIG. 1 or may be generated using a synthetic peptide (see above) which has a sequence inclusive of all of the common sequence features of the known 'death domain' motif sequences, e.g. the above mentioned amino acid residues W, L, I, A, D, E, T, R and Y.

The so-generated complementary peptides, and likewise, DNA sequences encoding them, which may be readily produced by standard procedures, may be employed, as noted above in any one of uses (i)–(vi), i.e. to enhance (gain-of-function) or inhibit the activity of proteins or receptors containing a 'death domain' motif, or may be used to generate specific antibodies thereto for modulation/mediation, isolation or diagnostic purposes.

It should also be noted that included in the present invention are the antibodies (and their uses) specific to the proteins and peptides of the invention including the complementary peptides, as well as antibodies specific to the 'death domain' motif peptides themselves, e.g. those peptides shown in FIG. 1 which are the 'death domain' motifs of p55-TNF-R, FAS-R, MORT-1, NGF-R, ankyrin 1 and other proteins containing the 'death domain' motif. These antibodies may be used for directly modulating/mediating the activity of proteins or receptors containing 'death domain' motifs or for isolation, identification and characterization (including diagnostic applications, as noted above) of other proteins and receptors containing such 'death domain' motifs.

As regards the antibodies mentioned herein throughout, the term "antibody" is meant to include polyclonal antibodies, monoclonal antibodies (mAbs), chimeric antibodies, anti-idiotypic (anti-Id) antibodies to antibodies that can be labeled in soluble or bound form, as well as fragments thereof provided by any known technique, such as, but not limited to enzymatic cleavage, peptide synthesis or recombinant techniques.

Polyclonal antibodies are heterogeneous populations of antibody molecules derived from the sera of animals immunized with an antigen. A monoclonal antibody contains a substantially homogeneous population of antibodies specific to antigens, which populations contains substantially similar epitope binding sites. MAbs may be obtained by methods known to those skilled in the art. See, for example Kohler and Milstein, *Nature*, 256:495–497 (1975); U.S. Pat. No. 4,376,110;. Ausubel et al., eds., Harlow and Lane ANTIBODIES: A LABORATORY MANUAL, Cold Spring Harbor Laboratory (1988); and Colligan et al., eds., Current Protocols in Immunology, Greene publishing Assoc. and Wiley Interscience N.Y., (1992, 1993), the contents of which references are incorporated entirely herein by reference. Such antibodies may be of any immunoglobulin class including IgG, IgM, IgE, IgA, GELD and any subclass thereof. A hybridoma producing a mAb of the present invention mav be cultivated in vitro, in sint or in vivo. Production of high titers of mAbs ini vivo or in situ makes this the presently preferred method of production.

Chimeric antibodies are molecules different portions of which are derived from different animal species, such as those having the variable region derived from a murine mAb and a human immunoglobulin constant region. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al., *Proc. Natl. Acad. Sci. USA* 81:3273–3277 (1984); Morrison et al., *Proc. Natl. Acad Sci. USA* 81:6851–6855 (1984); Boulianne et al., *Nature* 312:643–646 (1984); Cabilly et al., European Patent Application 125023 (published Nov. 14, 1984); Neuberger et al., *Nature* 314:268–270 (1985); Taniguchi et al., European Patent Application 171496 (published Feb. 19, 1985); Morrison et al., European Patent Application 173494 (published Mar. 5, 1986); Neuberger et al., PCT Application WO 8601533, (published Mar. 13, 1986); Kudo et al., European Patent Application 184187 (published Jun. 11, 1986); Sahagan et al., *J. Immunol.* 137:1066–1074 (1986); Robinson et al., International Patent Application No. WO8702671 (published May 7, 1987); Liu et al., *Proc. Natl. Acad. Sci. USA* 84:3439–3443 (1987); Sun et al., *Proc. Natl. Acad. Sci USA* 84:214–218 (1987); Better et al., *Scieice* 240:1041–1043 (1988); and Harlow and Lane, ANTIBODIES: A LABORATORY MANUAL, supra. These references are entirely incorporated herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g. mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference.

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mAbs generated against the 'death domain' motif-containing peptides, 'death domain' -binding proteins or peptides, or 'death domain' -binding complementary peptides, analogs or derivatives thereof of the invention may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for an epitope of the above proteins, peptides, analogs or derivatives.

The anti-Id mAbs thus have their own idiotypic epitopes, or "idiotopes" structurally similar to the epitope being evaluated, such as GRB protein-α.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')$_2$ and other fragments of the antibodies useful in the present invention may be used for the detection and quantitation of the 'death-domain'-binding proteins or peptides according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable bf binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

The antibodies, including fragments of antibodies, useful in the present invention may be used to quantitatively or qualitatively detect the 'death domain' motif-binding proteins or peptides (including complementary peptides) in a sample or to detect presence of cells which express the 'death domain' motif-binding proteins or peptides of the present invention. This can be accomplished by immunofluorescence techniques employing a fluorescently labeled antibody (see below) coupled with light microscopic, flow cytometric, or fluorometric detection.

The antibodies (or fragments thereof) useful in the present invention may be employed histologically, as in immunofluorescence or immunoelectron microscopy, for in situ detection of 'death domain' motif-binding proteins or peptides of the present invention. In situ detection may be accomplished by removing a histological specimen from a patient, and providing the labeled antibody of the present invention to such a specimen. The antibody (or fragment) is preferably provided by applying or by overlaying the labeled antibody (or fragment) to a biological sample. Through the use of such a procedure, it is possible to determine not only the presence of the 'death domain' motif-binding proteins or peptides, but also its distribution on the examined tissue. Using the present invention, those of ordinary skill will readily perceive that any of wide variety of histological methods (such as staining procedures) can be modified in order to achieve such in sits detection.

Such assays for 'death domain' motif-binding proteins of the present invention typically comprises incubating a biological sample, such as a biological fluid, a tissue extract, freshly harvested cells such as lymphocytes or leukocytes, or cells which have been incubated in tissue culture, in the presence of a detectably labeled antibody capable of identifying the 'death domain' motif-binding proteins or peptides, and detecting the antibody by any of a number of techniques well known in the art.

The biological sample may be treated with a solid phase support or carrier such as nitrocellulose, or other solid support or carrier which is capable of immobilizing cells, cell particles or soluble proteins. The support or carrier may then be washed with suitable buffers followed by treatment with a detectably labeled antibody in accordance with the present invention, as noted above. The solid phase support or carrier may then be washed with the buffer a second time to remove unbound antibody. The amount of bound label on said solid support or carrier may then be detected by conventional means.

By "solid phase support" , "solid phase carrier", "solid support", "solid carrier", "support" or "carrier" is intended any support or carrier capable of binding antigen or antibodies. Well-known supports or carriers, include glass, polystyrene, polypropylene, polyethylene, dextran, nylon amylases, natural and modified celluloses, polyacrylamides, gabbros and magnetite. The nature of the carrier can be either soluble to some extent or insoluble for the purposes of the present invention. The support material may have virtually any possible structural configuration so long as the coupled molecule is capable of binding to an antigen or antibody. Thus, the support or carrier configuration may be spherical, as in a bead, cylindrical, as in the inside surface of a test tube, or the external surface of a rod. Alternatively, the surface may be flat such as a sheet, test strip, etc. Preferred supports or carriers include polystyrene beads. Those skilled in the art will know may other suitable carriers for binding antibody or antigen, or will be able to ascertain the same by use of routine experimentation.

The binding activity of a given lot of antibody, of the invention as noted above, may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which an antibody in accordance with the present invention can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorometric or by visual means. Enzymes which can be used detectably label the antibody include, but are not limited to, malate dehydrozenase, staphylococcal nuclease, delta-5-steroid isomeras, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by calorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactivity labeling the antibodies or antibody fragments, it is possible to detect R-PTPase through the use of a radioimmnunoassay (RIA). A good description of RIA may be found in Laboratory Techniques and Biochemistry in Molecular Biology, by Work, T. S. et al., North Holland Publishing Company, NY (1978) with particular reference to the chapter entitled "An Introduction to Radioimmune Assay and Related Techniques" by Chard, T., incorporated by reference herein. The radioactive isotope can be detected by such means as the use of a γ counter or a scintillation counter or by autoradiography.

It is also possible to label an antibody in accordance with the present invention with a fluorescent compound. When the fluorescently labeled antibody is exposed to light of the proper wavelength, its presence can be then detected due to fluorescence. Among the most commonly used fluorescent labeling compounds are fluorescein isothiocyanate, rhodamine, phycoerythrine, pycocyanin, allophycocyanin, o-phthaldehyde and fluorescamine.

The antibody can also be detectably labeled using fluorescence emitting metals such as $^{152}$E, or others of the lanthanide series. These metals can be attached to the antibody using such metal chelating groups as diethylenetriamine pentaacetic acid (ETPA).

The antibody can also be detectably labeled by coupling it to a chemiluninescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An antibody molecule of the present invention may be adapted for utilization in an inmmunometric assay, also known as a "two-site" or "sandwich" assay. In a typical immunometric assay, a quantitv of unlabeled antibody (or fragment of antibody) is bound to a solid support or carrier and a quantity of detectably labeled soluble antibody is added to permit detection andlor quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support or carrier is washed to remove the residue of the fluid sample, including unreacted antigen, if any, and the contacted with the solution containing an unknown quantity of labeled antibody (which functions as a "reporter molecule"). After a second incubation period to permit the labeled antibody to complex with the antigen bound to the solid support or carrier through the unlabeled antibody, the solid support or carrier is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support or carrier and labeled antibody are both added to the sample being tested at the same time. After the incubation is completed, the solid support or carrier is washed to remove the residue of fluid sample and uncomplexed labeled antibody. The presence of labeled antibody associated with the solid support or carrier is then determined as it would be in a conventional "forward" sandwich assay.

In the "reverse" assay, stepwise addition first of a solution of labeled antibody to the fluid sample followed by the addition of unlabeled antibody bound to a solid support or carrier after a suitable incubation period is utilized. After a second incubation, the solid phase is washed in conventional fashion to free it of the residue of the sample being tested and the solution of unreacted labeled antibody. The determination of labeled antibody associated with a solid support or carrier is then determined as in the "simultaneous" and "forward" assays.

The new proteins and peptides of the invention once isolated, identified and characterized by any of the standard screening procedures, for example, the yeast two-hybrid method, affinity chromatography, and any other well known method known in the art, may then be produced by any standard recombinant DNA procedure (see for example, Sambrook, et al., 1989) in which suitable eukaryotic or prokaryotic host cells are transformed by appropriate eukaryotic or prokaryotic vectors containing the sequences encoding for the proteins. Accordingly, the present invention also concerns such expression vectors and transformed hosts for the production of the proteins of the invention. As mentioned above, these proteins also include their biologically active analogs and derivatives, and thus the vectors encoding them also include vectors encoding analogs of these proteins, and the transformed hosts include those producing such analogs. The derivatives of these proteins are the derivatives produced by standard modification of the proteins or their analogs, produced by the transformed hosts.

In another aspect, the present invention relates to the use of the various different 'death domain' motifs or the synthetically produced "universal" 'death domain' motif (having structural features common to many different 'death domain' motifs) as agents for enhancing (gain of function) the intracellular effect mediated by the natural 'death domain' motif-containing proteins. In this aspect the 'death domain' motifs will be used in the form of peptides containing all of the 'death domain' motif or active parts thereof and introduced into the cells as mentioned above (e.g. the vaccinia virus approach). In this regard it should be noted that the term 'death domain' was coined following the discovery (see the co-pending patent applications noted above) that this region of the intracellular domains of the p55 TNF-R and FAS-R was the region involved in the ligand-independent self-association and cell-cytotoxicity induction mediated by these receptors. In fact, the free 'death domain' of p55 TNF-R (p55DD) is capable of self-associating and inducing cell cytotoxicity. Further, upon discovery of the MORT1 protein which is a FAS-R binding protein, it was also found that this protein is capable of self-association and inducing, in a ligand-independent and FAS-R-independent manner, cytotoxic effects on cells. The MORT-1 protein was subsequently observed to contain a 'death domain' motif homologous to the 'death domains' or 'death domain' motifs of p55 TNF-R and FAS-R (see FIG. 1), which 'death domain' motif is involved in MORT1 association with FAS-R and is associated with the MORT1 protein's ability to induce cell cytotoxic effects.

Thus, using the 'death domain' motifs of proteins such as p55-TNF-R, FAS-R and MORT1 and any other proteins involved in the induction of cytotoxic effects, in the way described above, it is possible to enhance the cell cytotoxic effects normally mediated by the naturally-occuring counterparts of these proteins, i.e. it would be possible to enhance the killing of cells such as tumor cells, HTV-infected and other diseased cells, the killing of which is usually mediated by p55 TNF-R, FAS-R, MORT1, RIP or TRADD, by introducing into such cells the 'death domain' motifs of these receptors/proteins.

Moreover, it is also possible to produce analogs of these 'death domain' motifs which will provide an even better enhancement of their action, i.e. enhanced cell cytotoxicity, these analogs having one or more amino acids added, deleted or replaced with respect to the naturally occuring sequences.

In a similar fashion it is also possible by the means described herein above to introduce 'death domain' motifs or analogs thereof, of the NGF-R or ankyrin 1 into cells in which it is desired to enhance the intracellular effects mediated by NGF-R or ankyrin-1.

Likewise, the present invention also relates to the specific blocking of the effects mediated by the 'death domain' motif-containing proteins by blocking the activity of the 'death domain' motifs of these proteins, e.g. by the introduction of anti-sense oligonucleotides into cells (as mentioned above) which would block the expression of the 'death domain' motifs.

In yet another aspect of the invention there is provided organic compounds, e.g. heterocyclic compounds, which are capable of specifically binding to the 'death domain' motifs of one or more 'death domain' motif-containing proteins. These organic compounds are well known in the field of pharmaceuticals and are widely used as therapeutic agents which are capable of entering cells (hydrophobicilipophilic compounds) and binding various intracellular proteins or intracellular portions of transmembrane proteins and thereby exerting their effect. These organic compounds may be readily screened and identified by using the 'death domain' motifs of the death domain motif-containing proteins, e.g. those of p55 TNF-R, FAS-R. NGF-R, MORT1, ankyrin 1, in standard affinity chromatography procedures or other methods well known in the art.

It should also be mentioned, that the 'death domain' motif consists of both general structural features common to all of the various such motifs, i.e. a common scaffold, as well as specific structural features, specific to each of the 'death domain' motifs. Accordingly, a preferred drug or pharmaceutically active molecule according to the invention will contain, as active ingredient, naturally occurring proteins or peptides; synthetically produced proteins or peptides including complementary peptides; antibodies; or chemical compounds obtained by screening or design, all of which are characterized by being capable of recognizing the general 'death domain' features and one or more of the specific 'death domain' features.

The present invention also relates to pharmaceutical compositions comprising recombinant animal virus vectors encoding the 'death domain' motif-binding proteins or peptides or the 'death domain' motif sequences themselves, which vector also encodes a virus surface protein capable of binding specific target cell (e.g. cancer cells) surface proteins to direct the insertion of the 'death domain' motif-binding protein or peptide sequences or the 'death domain' motif sequences into the cells. Likewise, the present invention also relates to pharmaceutical compositions comprising organic compounds capable of binding to 'death domain' motifs of 'death domain' motif-containing proteins.

The invention will now be described in more detail in the following non-lirmiting examples and the accompanying drawings:

EXAMPLE 1

The 'Death Domain' Motif Common to the Receptors p55 TNF-R. FAS-R and NGF-R and to the Proteins MORT1 and Ankyrin 1

Upon the discovery of MORT1 (see co-pending IL 109632, IL 112002 and 112692) it was also discovered that MORT1 contains a region having homology to the previously identified 'death domains' of p55 TNF-R and FAS-R (p55DD and FAS-DD, respectively), see IL 109632 and IL 111125). This surprising discovery of a 'death domain' motif in a previously unknown protein led to a search for the existence of such a 'death domain' motif in other proteins. Surprisingly, such a 'death domain' motif was discovered in the low affinity NGF-R and in an apparently unrelated, cytoskeletal protein, ankyrin 1. The 'death domain' motifs of all these different proteins share a remarkable homology as is set forth schematically in FIG. 1, which shows a sequence comparison of the 'death domain' motifs of the p55 TNF-R, FAS-R, MORT1, low affinity NGF-R and the C terminal part of the regulatory domain in ankyrin 1 (all of human origin). The homology of these 'death domain' motifs was defined by the LINEUP and PRETTY programs of the GCG package. Identical and similar residues in three or more of the proteins are boxed. Gaps introduced to maximize alignment are denoted by dots. The significance of this homology was confirmed as follows : (a) Multiple alignment of the 'death domain' motif sequences, using the HSSP program of the PredictProtein Service (Sander and Schneider, 1991) showed sequence identities of 21–38% and sequence similarities of 3048%. (b) Searching the Swiss-Prot data bank with a profile created (using the PILEUP, LINEUP and PROFILEMAKE programs of the GCG package) from consensuses of the 'death domain' motif sequences in the known p55 R and FAS-R (human, mouse, rat), NGF receptor (human, rat and chicken) and ankyrins (human and mouse ankyrin 1 and the human ankyrins c and g) sequences and in MORT1 yielded high scores only those sequences that were used for creating the profile (Zscores>8.5 for all of them in search with the "Bioaccelerator" Compugen, Israel).

The above homology search using the PredictProtein Service (PHDsec) and the PRODOM program of the GCG package revealed significant similarity between a region of approximately 65 residues in MORT1. within that part of the molecule that binds to FAS-R, and a region of that same length within the 'death domains' of FAS-R and p55-R, (FIG. 1). This part of the 'death domain' also shows similarity to a region in the intracellular domain of the low-affinity NGF receptor (Johnson et al., 1986), a receptor whose extracellular domain is known to contain another conserved sequence motif common to FAS-R, the TNF-Rs and other members of the TNF/NGF receptor fanily. It also revealed a previously-unnoticed similarity between this part of the 'death domain' and a conserved region in the ankyrins, which are structural proteins that link spectrin-based membrane skeletal proteins to the cytoplasmic domains of integral plasma membrane proteins (Lux et al., 1990; Lambert and Bennett, 1993). That region is located in the N terminal part of the ankyrin regulatory domain, just upstream to that part of the domain whose expression in subject to modulation by alternative splicing, and below the spectrin-binding and membrane binding domains. (The latter domain contains another known sequence motif—the 'ankvrin repeat'). The 'death domain' motif is distinct from the ankyrin repeat motif that is found in the membrane binding domain of the ankyrins.

The finding of a 'death domain' motif in proteins having different intracellular effects suggests that this motif plays a more general role than that implied in the name 'death domain' , i.e. this motif occurs in receptors such as p55 TNF-R, FAS-R and the related protein MORT1 which mediate cell cytotoxicity, as well as in the NGF-R which, when inducing death does so only in the absence of ligand (Rabizadeh et al., 1993) and in proteins such as the cytoskeletal ankyrins, not associated with cell cytotoxic effects. One kind of general activity of this 'death domain' motif, found so far in three of the proteins containing it, i.e. FAS-R, p55 TNF-R and MORT1 is the ability to self-associate or interact with other proteins that contain this motif.

The discovery of the 'death domain' motif in such a wide range of different proteins provides the way for obtaining (as noted herein above and in Example 2 below) proteins or peptides capable of binding to the different (one or more) 'death domain' motifs, which proteins and peptides may be used as modulators/mediators of a wide group of regulatory proteins, be they cytokine receptors involved in cell cytotoxic (p55 TNF-R, FAS-R) or growth (NGF-R) effects or related proteins involved in cell cytotoxic effects (MORT1) or regulatory portions of structural proteins involved in the shape/conformational regulation of cells (ankyrins). In a similar fashion, the 'death domain' motifs of these various proteins may also be used directly for modulation/mediation of proteins containing such motifs.

EXAMPLE 2

Interaction of 'Death Domains' of Human p55-TNF-R, FAS-R, TRADD, MORT-1 and RIP a) Experimental Procedures Two hybrid β-galactosidase expression tests—cDNA inserts were cloned by PCR, either from the full-length cDNAs cloned previously in our laboratory, or from purchased cDNA libraries. Residue numbering in the proteins encoded by the cDNA inserts are as in the Swiss-Prot Data Bank. Point mutants were produced by oligonucleotide-directed mutagenesis (Kunkel, 1994). β-galactosidase expression in yeasts (SFY526 reporter strain (Bartel et al., 1993)) transformed with these cDNAs in the pGBT-9 and pGAD-GH vectors (DNA binding domain (DBD) and activation domain (AD) constructs, respectively) was assessed by a filter assay (Boldin et al., 1995). When expressed in the pGAD-GH vector, RIP and its DD had some cytotoxic effect on the yeasts, manifested in a low yield of yeast colonies. They did not have any such cytotoxic effect when expressed (to a lower extent) in the pGBT-9 vector.

Induced expression, metabolic labeling and immunoprecipitation of proteins—Since the size similarity of the DDs makes it difficult to distinguish between them in gel electrophoresis, we chose to examine the interaction of MORT-1, TRADD and RIP by co-expressing the full-length MORT-1 protein with the DDs of TRADD and RIP. The proteins, N-linked to the FLAG octapeptide (Eastman-Kodak, New Haven, Conn.), or to an influenza hemagglutinin epitope (HA epitope, (Field et al., 1988)) were expressed in HeLa cells, using a tetracycline-controlled expression vector, and labeled metabolically with [$^{35}$S]-Met (55 $\mu$Ci/ml) and [$^{35}$S]-Cys (10 $\mu$Ci/ml) (EXPRE$^{35}$S$^{35}$S Protein Labeling Mix, DuPont, Wilmington. Del.), as described before (Boldin et al.. 1995). The cells were then lysed in RIPA buffer (1 ml/5×10$^5$ cells) and the lysates were precleared by incubation with irrelevant rabbit antiserum (3 $\mu$l/ml) and Protein G Sepharose beads (Pharmacia, Uppsala, Sweden; 6- $\mu$l/ml). Immunoprecipitation was performed by 1 h. incubation at 4° C. of 0.3 ml aliquots of lysate with mouse monoclonal antibodies (5 $\mu$g/aliquot) against the FLAG octapeptide (M2; Eastman Kodak). HA epitope (12CA5 (Field et al., 1988)), or the p75 TNF-R (#9; (Bigda et al., 1994)) as a control, followed by an additional 1 h. incubation with Protein G Sepharose beads (30 $\mu$l/aliquot). The immunoprecipitates were washed 3 times with RIPA buffer and analyzed by SDS-polyacrylamide gel electrophoresis.

b) Evaluation

The interactions of the DDs of human p55 TNF-R, FAS-R, TRADD, MORT-1 and RIP were evaluated first by a yeast two-hybrid test. The cDNAs encoding these domains were expressed as fusion proteins with the Gal4 DNA binding and activation domains (DBD and AD constructs) in the yeast SFY526 reporter strain, and the binding of these fusion proteins to each other was assessed by determining β-galactosidase expression by the yeasts. The results of these tests are summarized in FIG. 1 and illustrated diagrammatically in FIG. 3.

The DDs of p55 TNF-R, FAS-R, TRADD and RIP were able to self-associate. The DD of MORT-1 lacked this ability, even though the full length MORT-1 protein does self-associate (Boldin et al., 1995), apparently through an interaction that involves the region upstream of its DD.

The DD of TRADD bound to the DD of p55 TNF-R, but not to the DD of FAS-R, while the DD of MORT-1 behaved in the converse fashion.

The DD of RIP, like the full length RIP protein (Stanger et al., 1995), was able to bind both to the DDs of FAS-R and p55 TNF-R. Binding was significantly weaker, though, than that of the DDs of TRADD and MORT-1 to these receptors. Although RIP wa initially identified by virtue of its binding in a two-hybrid screen to FAS-R (Stanger et al., 1995), this binding is quite weak, and could be observed only when the RIP DD was highly expressed in the yeasts, by introducing it into the AD construct. There was no measurable binding when the DD of RIP was introduced into the DBD construct, which has a lower expression effectivity. A longer RIP insert, corresponding to amino acids 161–372 in the protein, did not bind more effectively to FAS-R (not shown).

Apart from their observed binding to the DDs of P55 TNF-R or FAS-R, the DDs of each of the three intracellular proteins tested bound also to each other. These interactions were all effective. Notably, the effectivity of binding of the DD of RIP to the DDs of MORT-1 and TRADD was significantly greater than that of its binding to the DDs of p55 TNF-R and FAS-R.

A similar pattern of interaction was observed in the HF7c yeast reporter strain, regularly used in inventors' laboratory for two-hybrid screens. Indeed, in a recent attempt to clone proteins that bind to MORT-1 by a two-hybrid screen, it was found that a significant proportion of the cloned cDNAs encode TRADD or RIP (not shown).

In specificity tests for the two-hybrid assay, we did not observe binding of the DD motifs to any of a number of irrelevant proteins, including SNF 1, the intracellular domain of the human p75 TNF receptor, lamin, cycline D and the DD of the rat low-affinity NGF receptor (not shown). To further assess the binding specificity, we introduced point mutations to the p55 TNF-R, FAS-R, MORT-1 and RIP DDs, at sites corresponding to that of I-225 in the mouse FAS-R sequence. A natrually occurring replacement mutation of this residue, found in lpr$^{c\ g}$ mice, abolishes signaling by FAS-R (Itoh and Nagata, 1993; Watanabe-Fukunaga et al., 1992) as well as its interaction with MORT-1 (Boldin et al., 1995; Chinnalyan et al., 1995). Mutation of the corresponding residues in the DDs of human p55 TNF-R (L351N) and FAS-R (V238N) had a similar effect. The mutated proteins were not able to self-associate, nor to bind to TRADD, MORT-1 or RIP. Also, introduction of a replacement mutation to the DD of RIP at the site corresponding to that of the lpr$^{c\ g}$ mutation (F308N) resulted in loss of its ability to bind to FAS-R, MORT-1 and TRADD, as well as to self-associate, although the mutated protein bound to the normal RIP DD. On the other hand, in MORT-1 the lpr$^{c\ g}$ like mutation (V121N) had only a limited effect. It resulted in less effective binding to FAS-R which, for some reason, was observed only when the mutated protein was introduced into the AD construct but not in the DBD construct.

Figure 4:
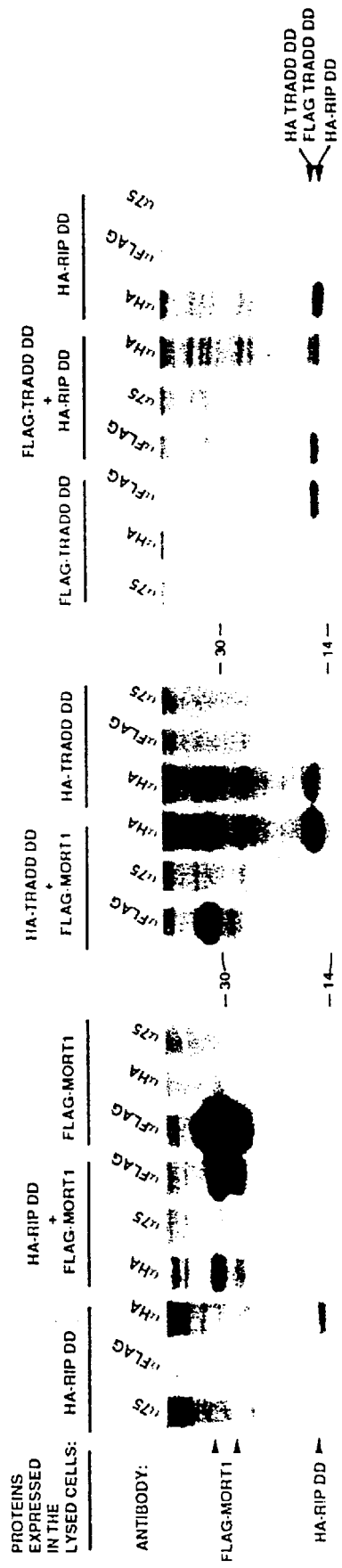
FIG. 4 depicts interactions of MORT-1, TRADD and RIP within transfected HeLa cells. MORT-1 (nucleotides 19–753 in GenBank accession number U2423 1), fused at is N-terminus with the FLAG octapeptides, and the DDs of TRADD (amino acids 195–312) and of RIP (amino acids 261–372), fused at their N-termini either with the FLAG octapeptide or the HA epitope (Field et al., 1988), were expressed, either alone or in mixtures of two in HeLa cells and metabolically labeled with [$^{35}$S]-Cys and [$^{35}$S]-Met. Cross-immunoprecipitation of the co-expressed proteins was performed using the indicated antibodies. The proteins were analyzed by SDS-polyacrylamide gel electrophoresis (15% acrylamide), followed by autoradiography. In cell lysates containing MORT-1 and RIP co-immunoprecipitation of both proteins could be obtained using antibodies against either one of them. However, in lysates containing TRADD anmd RIP, co-immunoprecipitation of the two proteins was observed only when using antibody against RIP, and in lysates containing TRADD and MORT-1 - only with an antibody against TRADD, apparently due to steric hindrance.

To test whether the interactions observed between TRADD, MORT-1 and RIP in the yeast two-hybrid tests occur also in eukaryotic cells, we co-expressed MORT-1 and the DDs of TRADD and RIP within transfected HeLa cells and attempted to immunoprecipitate them from the cell lysates. Immunoprecipitation resulted in precipitation of the co-expressed proteins, indicating that they bind to each other within the HeLa Cells (FIG. 4).

Although the evidence is still largely indirect, TRADD, MORT-1 and RIP appear to play important roles in the initiation of the cytocidal effect of p55 TNF-R and FAS-R (Cleveland and Ihle, 1995). The binding of these proteins to the receptors, which occurs through their DDs, apparently is required for their contribution to the signaling. A recent study showing that stimulation of FAS-R in cells evokes binding of MORT-1 to this receptor suggests that the DD interactions observed within transfected yeasts also occur within the mammalian cells, and take part in the process of signaling induction (Kischkel et al., 1995). Although the DDs of all the proteins examined have the ability to bind to other DDs, there is clear specificity in this interaction. The DD of TRADD binds to that of p55 TNF-R, but not to the DD of FAS-R. The DD of MORT-1 binds to the DD of FAS-R, but does not bind to the DD of p55 TNF-R. This specificity in the action of proteins that take part in the signaling activity of p55 TNF-R and FAS-R may well contribute to the differences in function of the two receptors.

In addition to their differential binding to the DDs of p55 TNF-R and FAS-R, the DDs of TR ADD and MORT-1 also are able to bind effectively to each other, and both are capable of binding to the DD of REP more effectively than do the DDs of FAS-R or p55 TNF-R. Thus, even though distinct, the signaling cascades affected by TRADD and MORT-1 may well turn to be coordinated through their mutual interactions. The nature of this coordination may vary, depending on the way in which the different interactions of the DD in a given protein affect each other. These interactions may occur together or be exclusive; they may also modulate each other. One possible way for such modulation is indicated by the occurrence in RIP of sequence motifs characteristic of protein kinases. If this protein indeed possesses protein kinase activity, it may turn to be capable of phosphorylating MORT-1 and TRADD upon binding to them, thereby modulating their function. One plausible consequence of the association of TRADD and MORT-1, and of the binding of RIP to both proteins, is integration of their effects, at least in part. This integration may account for the fact that cell death induction by p55 TNF-R and FAS-R exhibit, alongside distinct features, also certain similarities; this could result also in sharing of other activities of the two receptors.

EXAMPLE 3

Cloning and Isolation of Proteins which Bind to the 'Death Domain' Motifs of 'Death Domain' Motif-containing Proteins To isolate proteins interacting with the 'death domain' motifs of 'death domain' motif-containing proteins, for example, the 'death domain' motifs of p55 TNF-R, FAS-R, NGF-R, MORT1 and ankyrin t, the yeast two-hybrid system (Fields and Song, 1989) may be used as described in co-pending Israel patent application Nos. 109632, 112002 and 112692. Briefly, this two-hybrid system is a yeast-based genetic assay to detect specific protein-protein interactions in vivo by restoration of a eukaryotic transcriptional activator such as GAL4 that has two separate domains, a DNA binding and an activation domain, which domains when expressed and bound together to form a restored GAL4 protein, is capable of binding to an upstream activating sequence which in turn activates a promoter that controls the expression of a reporter gene, such as lacZ or HIS3, the expression of which is readily observed in the cultured cells. In this system the genes for the candidate interacting proteins are cloned into separate expression vectors. In one expression vector the sequence of the one candidate protein is cloned in phase with the sequence of the GAL4 DNA-binding domain to generate a hybrid protein with the GAL4 DNA-binding domain, and in the other vector the sequence of the second candidate protein is cloned in phase with the sequence of the GAL4 activation domain to generate a hybrid protein with the GAL4-activation domain. The two hybrid vectors are then co-transformed into a yeast host strain having a lacZ or HIS3 reporter gene under the control of upstream GAL4 binding sites. Only those transformed host cells (cotransformants) in which the two hybrid proteins are expressed and are capable of interacting with each other, will be capable of expression of the reporter gene. In the case of the lacz reporter gene, host cells expressing this gene will become blue in color when X-gal is added to the cultures. Hence, blue colonies are indicative of the fact that the two cloned candidate proteins are capable of interacting with each other.

Using this two-hybrid system, the 'death domain' motifs may be cloned, separately, into the vector pGBT9 (carrying the GAL4 DNA-binding sequence, provided by CLONTECH, USA, see below), to create fusion proteins with the GAL4 DNA-binding domain. Once the sequence of the 'death domain' motif is known, e.g. those shown in FIG. 1, the DNA sequence encoding these motifs may be readily isolated and cloned, by standard procedures into the pGBT9 vector utilizing the vector's multiple cloning site region (MCS).

The above hybrid (chimeric) pGBT9 vectors can then be cotransfected (separately, one cotransfection with each 'death domain' motif-containing hybrid together with a cDNA or genomic DNA library from human or other mammalian origin, e.g. a cDNA library from human HeLa cells cloned into the pGAD GH vector, bearing the GAL4 activating domain, into the HF7c yeast host strain (all the above-noted vectors, pGBT9 and pGAD GH carrying the HeLa cell cDNA library, and the yeast strain are purchasable from Clontech Laboratories, Inc., USA, as a part of MATCHMAKER Two-Hybrid System, #PT1265-1). The co-transfected yeasts are then selected for their ability to grow in medium lacking Histidine (His⁻ medium), growing colonies being indicative of positive transformants. The selected yeast clones were then tested for their ability to express the lacZ gene, i.e. for their LAC Z activity, and this by adding X-gal to the culture medium, which is catabolized to form a blue colored product by β-galactosidase, the enzyme encoded by the lacZ gene. Thus, blue colonies are indicative of an active lacZ gene. For activity of the lacZ gene, it is necessary that the GAL4 transcription activator be present in an active form in the transformed clones, namely that the GAL4 DNA-binding domain encoded by one of the above hybrid vectors be combined properly with the GAL4 activation domain encoded by the other hybrid vector. Such a combination is only possible if the two proteins fused to each of the GAL4 domains are capable of stably interacting (binding) to each other. Thus, the His⁺ and blue (LAC Z⁺) colonies that are isolated are colonies which have been cotransfected with a vector encoding a 'death domain' motif and a vector encoding a protein product of, for example, human HeLa cell origin that is capable of binding stably to a 'death domain' motif.

The plasmid DNA from the above His⁺, LAC Z⁺ yeast colonies can then be isolated and electroporated into $E.\ coli$ strainHB101 by standard procedures followed by selection of Leu⁺ and Ampicillin resistant transformants, these transformants being the ones carrying the hybrid pGAD GH vector which has both the $Amp^R$ and $Leu^2$ coding sequences. Such transformants therefore are clones carrying the sequences encoding newly identified proteins or peptides capable of binding to the 'death domain' motifs. Plasmid DNA was then isolated from these transformed $E.\ coli$ and retested by:

(a) retransforming them with the original 'death domain' motif-containing hybrid plasmids into yeast strain HFU7 as set forth hereinabove. As controls, vectors carrying irrelevant protein encoding sequences, e.g. pACT-lamin or pGBT9 alone can be used for cotransformation with the 'death domain' motif-binding protein or peptide encoding plasmids. The cotransformed yeasts can then be tested for growth on His⁻ medium alone, or with different levels of 3-aminotriazole; and (b) retransforming the plasmid DNA and original 'death domain' motif hybrid plasmids and control plasmids described in (a) into yeast host cells of strain SFY526 and determining the LAC Z⁺ activity (effectivity of β-gal formation, i.e. blue color formation). It should be noted that the above noted β-galactosidase (β-gal) expression tests can also be done by a standard filter assay.

EXAMPLE 4

Assessment of the Involvement of Sequence Features Characteristic of the 'Death Domain' Motif in the Binding of the Cloned Proteins The cDNA encoding the protein that contains the 'death domain' motif will be mutated at the various amino acids that constitute this motif. For example, tryptophan 380 in the intracellular domain of the human low-affinity nerve growth factor receptor (NGF-R) will be replaced with alanine. Such mutation can be performed, for example, by the Kunkel oligonucleotide-directed mutagenesis procedure. The mutated, as well as the wild-type proteins, can be produced in bacteria as fusions with Glutathione S-transferase (GST). The binding of the cloned protein in vitro to the GST fusion with the mutated NGF-R will be compared to its binding to the GST-wild type NGF-R intracellular domain fusion. Abolition of the binding by the mutation will indicate that the cloned protein indeed recognizes sequence features that are involved in the 'death domain' motif. A similar approach will be taken to assess the involvement of the sequence features characteristic of the 'death domain' in the function of other reagents that interact with proteins containing this motif, namely antibodies, peptides or organic compounds (See Example 4).

EXAMPLE 5

Design of Drugs that Affect 'Death Domain' Motif-containing Proteins by Virtue of their Ability to Interact with the 'Death Domain'

Organic molecules or peptides that interact with the 'death domain' motif of one of the proteins containing this motif will be defined either by screening or by design. Further changes will then be introduced to this molecule to increase the effectivity of its interaction with that specific 'death domain' and the ability of the designed compound to affect (enhance or interfere with) the function of the protein containing the 'death domain'. Once creating such a molecule and defining the sequence feature of the 'death domain' which it recognizes (see Example 3) as well as the conformational features of the 'death domain' involved in this recognition (by NMR, X-ray crystallography, etc.), this knowledge can be applied as a starting point for designing drugs that will affect other proteins containing the 'death domain' motif. To do so, one should introduce to the designed peptide or organic molecule, besides structural features that allow recognition of those structural features that are common to the 'death domain', also structural features that will dictate specific recognition of the specific 'death domain' containing protein.

EXAMPLE 6

Analysis of the Biological Activity of the 'Death Domain' Motif Binding Proteins, Peptides, Antibodies or Organic Molecules Once the 'death domain' motif binding proteins or peptides have been isolated, e.g. by the procedure of Example 1, they can be tested for their biological activity. In co-pending applications IL 109632, 111125, 112002 and 112692, there is described one such procedure which assays the effect of intracellular domain binding proteins of the cytotoxic effects mediated by the p55 TNF-R, FAS-R and MORT1 (HF1).

Thus, using similar procedures it is possible to determine, firstly, the ability of such 'death domain' motif-binding proteins or peptides to associate in vitro with 'death domain' motif-containing proteins such as p55 TNF-R, FAS-R, NGF-R, MORT-1, RIP, TRADD and ankyrin 1; and secondly to assess in vivo, using standard cell cytotoxicity assays, whether such 'death domain' motif binding proteins or peptides are capable of enhancing or inhibiting the cell cytotoxicity induced by such receptors as p55 TNF-R or FAS-R or proteins such as MORT1.

Likewise, the same tests may also be applied to assay organic compounds (obtained by screening or design, see Example 4); synthetically produced peptides (see Example 4); and antibodies, capable of binding to 'death domain' motifs.

REFERENCES

Barinaga, M. (1993) Science 262:1512–4.
Bartel, P. L. et al. (1993) Bio Techniques 14:920–924.
Beutler, B. and Cerami, C. (1987) NEYM, 316:379–385.
Bigda, J. et al. (1994) J. Exp. Med. 180:445–460.
Boldin, M. P. et al. (1995) J. Biol. Chem. 270, 337–341.
Boldin, M. P. et al. (1995) J. Biol. Chem. 270, 387–391.
Boldin, M. P. et al. (1995) J. Biol. Chem. 270 7795–8.
Brakebusch, C. et al. (1992) EMBO J., 11:943–950.
Brockhaus, M. et al. (1990) Proc. Natl. Acad. Sci. USA, 87:3127–3131.
Cantor, G. H. et al. (1993) Proc. Natl. Acad. Sci. USA 90:10932–6.
Chen, C. J. et al. (1992) Ann N.Y. Acad. Sci. 660:271–3.
Chinnalyan, A. M. et al (1995) Cell 81:505–512.
Cleveland, J. L. and Ihle, J. N. (1995) Cell 81:479–482.
Crisell, P. et al., (1993) Nucleic Acids Res. (England) 21 (22):5251–5.
Engelmann, H. et al. (1990) J. Biol. Chem., 265:1531–1536.
Field, J. et al. (1988) Molec. Cell. Biol. 8:2159–2165.
Fields, S. and Song, O. (1989) Nature, 340:245–246.
Heller, R. A. et al. (1990) Proc. Natl. Acad. Sci. USA, 87:6151–6155.
Hohmann, H.-P. et al. (1989) J. Biol. Chem., 264:14927–14934.
Hsu, H. et al., (1995) Cell 81: 495–504.
Itoh, N. et al. (1991) Cell 66:233.
Itoh, N. and Nagata, S. (1993) J. Biol. Chem. 268 10932–7.
Johnson, D. et al. (1986) Cell 47. 545–554.
Joseph, S. and Burke, J. M. (1993) J. Biol. Chem. 268:24515–8.
Kischkel, F. C. et al. (1995) EMBO J. (in press)
Koizumi, M. et al. (1993) Biol. Pharm. Bull (Japan) 16 (9):879–83.
Kunkel, T. A. (1994) in *Current Protocols in Molecular Biology*, (Ausubel et al,.(eds)), pp. 8.1.1–8.1.6, Greene Publishing Associates, Inc. and Wiley & Sons, Inc., New York.
Lambert, S. and Bennet, V. (1993) Eur. J. Biochem. 211, 1–6.
Loetscher, H. et al. (1990) Cell, 61:351–359.
Lux, S. E. et al. (1990) Nature 344, 36–42.
Nophar, Y. et al. (1990) EMBO J., 9:3269–3278.
Piquet, P. F. t al. (1987) J. Exp. Med., 166:1280–89.
Rabizadeh, S. et al. (1993) Science 261, 345–348.
Sambrook et al. (1989) *Moleczlar Cloning: A Laboratory Manual,* Cold Spring Harbor Laboratory Press, Cold Spring Harbor, N.Y.
Sander, C. and Schneider, R. (1991) Proteins 9, 56–68.
Schall, T. J. et al. (1990) Cell, 61:361–370.
Shimayama, T. et al., (1993) Nucleic Acids Symp. Ser. 29:177–8
Shore, S. K. et al. (1993) Oncogene 8:3183–8.
Smith, C. A. et al. (1990) Science, 248:1019–1023.
Song, H. Y. et al. (1994) J. Biol. Chem. 269, 22492–22495.
Stanger, B. Z. et al. (1995) Cell 81.513–523.
Tartaglia, L. A. et al. (1993) Cell, 74:845–853.
Tracey, J. T. et al. (1987) Nature, 330:662–664.
Wallach, D. (1986) in: *Interferon* 7 (Ion Gresser, ed.), pp. 83–122, Academic Press, London
Wallach, D. et al. (1994) Cytokine 6, 556.
Watanabe-Fukunaga, R. et al. (1992) Nature, 356, 314–317.
Wilks, A. F. et al. (1989) Proc. Natl. Acad. Sci. USA, 86:1603–1607.
Zhao, J. J. and Pick, L. (1993) Nature (England) 365:448–51.

What is claimed is:

1. An antibody specific to the death domain of a death domain-containing regulatory protein selected from the group consisting of NGF-R, MORT-1 and ankyrin 1.

2. An antibody in accordance with claim 1, wherein said antibody is capable of binding to the death domain of more than one of said death domain-containing regulatory proteins.

3. An antibody in accordance with claim 1 comprising a fragment of an antibody specific to the death domain of one of said death domain-containing regulatory proteins, wherein said fragment is capable of binding said death domain.

4. An antibody in accordance with claim 2 comprising a fragment of an antibody specific to the death domain of one of said death domain-containing regulatory proteins, wherein said fragment is capable of binding the death domain of more than one of said death domain-containing regulatory proteins.

5. An antibody in accordance with claim 1 comprising a monoclonal antibody.

6. An antibody in accordance with claim 2 comprising a monoclonal antibody.

\* \* \* \* \*

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 63 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 1:

Val Lys Gly Phe Val Arg Lys Asn Gly Val Asn Glu Ala Lys Ile As

```
                   -continued
1               5                  10                 15
Glu Ile Lys Asn Asp Asn Val Gln Asp Thr Ala Glu Gln Lys Val Gl
            20                 25                30

Leu Leu Arg Asn Trp His Gln Leu His Gly Lys Lys Glu Ala Tyr As
            35                 40                45

Thr Leu Ile Lys Asp Leu Lys Lys Ala Asn Leu Cys Thr Leu Ala
    50                 55                60

(2) INFORMATION FOR SEQ ID NO: 2:

(i) SEQUENCE CHARACTERISTICS:
        (A) LENGTH: 63 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

Trp Ala Glu Leu Ala Arg Glu Leu Gln Phe Ser Val Glu Asp Ile As
1               5                  10                 15

Arg Ile Arg Val Glu Asn Pro Asn Ser Leu Leu Glu Gln Ser Val Al
            20                 25                30

Leu Leu Asn Leu Trp Val Ile Arg Glu Gly Gln Asn Ala Asn Met Gl
            35                 40                45

Asn Leu Tyr Thr Ala Leu Gln Ser Ile Asp Arg Gly Glu Ile Val
    50                 55                60

(2) INFORMATION FOR SEQ ID NO: 3:

(i) SEQUENCE CHARACTERISTICS:
        (A) LENGTH: 64 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Trp Lys Glu Phe Val Arg Arg Leu Gly Leu Ser Asp His Glu Ile As
1               5                  10                 15

Arg Leu Glu Leu Gln Asn Gly Arg Cys Leu Arg Glu Ala Gln Tyr Se
            20                 25                30

Met Leu Ala Thr Trp Arg Arg Thr Pro Arg Arg Glu Ala Thr Le
            35                 40                45

Glu Leu Leu Gly Arg Val Leu Arg Asp His Asp Leu Leu Gly Cys Le
    50                 55                60

(2) INFORMATION FOR SEQ ID NO: 4:

(i) SEQUENCE CHARACTERISTICS:
        (A) LENGTH: 56 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

Trp Arg His Leu Ala Gly Glu Leu Gly Tyr Gln Pro Glu His Ile As
1               5                  10                 15

Ser Phe Thr His Glu Ala Cys Pro Val Arg Ala Leu Leu Ala Ser Tr
            20                 25                30
```

```
Ala Thr Gln Asp Ser Ala Thr Leu Asp Ala Leu Leu Ala Ala Leu Ar
        35                  40                  45

Arg Ile Gln Arg Ala Asp Leu Val
        50                  55
```

(2) INFORMATION FOR SEQ ID NO: 5:

(i) SEQUENCE CHARACTERISTICS:
        (A) LENGTH: 62 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

```
Trp Arg Arg Leu Ala Arg Gln Leu Lys Val Ser Asp Thr Lys Ile As
1               5                   10                  15

Ser Ile Glu Asp Arg Tyr Pro Arg Asn Leu Thr Glu Arg Val Arg Gl
            20                  25                  30

Ser Leu Arg Ile Trp Lys Asn Thr Glu Lys Glu Asn Ala Thr Val Al
            35                  40                  45

His Leu Val Gly Ala Leu Arg Ser Cys Gln Met Asn Leu Val
        50                  55                  60
```